(12) United States Patent
Takahashi et al.

(10) Patent No.: US 9,284,260 B2
(45) Date of Patent: Mar. 15, 2016

(54) METHOD FOR PRODUCING RACEMATE OF COMPOUND

(71) Applicant: SUMITOMO CHEMICAL COMPANY, LIMITED, Tokyo (JP)

(72) Inventors: Tomoaki Takahashi, Oita (JP); Taro Hirose, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/439,597

(22) PCT Filed: Oct. 28, 2013

(86) PCT No.: PCT/JP2013/079655
§ 371 (c)(1),
(2) Date: Apr. 29, 2015

(87) PCT Pub. No.: WO2014/069611
PCT Pub. Date: May 8, 2014

(65) Prior Publication Data
US 2015/0266805 A1    Sep. 24, 2015

(30) Foreign Application Priority Data

Nov. 2, 2012  (JP) ................................. 2012-242487

(51) Int. Cl.
*C07C 209/68* (2006.01)
*C07B 55/00* (2006.01)
*C07C 209/82* (2006.01)

(52) U.S. Cl.
CPC ............... *C07C 209/68* (2013.01); *C07B 55/00* (2013.01); *C07C 209/82* (2013.01); *C07B 2200/07* (2013.01); *C07C 2102/08* (2013.01)

(58) Field of Classification Search
CPC   C07C 209/68; C07C 209/82; C07C 2102/08; C07B 55/00; C07B 2200/07
See application file for complete search history.

(56) References Cited

U.S. PATENT DOCUMENTS 8,173,849 B2 * 5/2012 Jenkins ................ A61K 9/0019
560/157
2009/0163719 A1   6/2009 Blacker et al.

FOREIGN PATENT DOCUMENTS

| EP | 2 891 647 A1 | 7/2015 |
| JP | 1-211568 A | 8/1989 |
| JP | 10-72410 A | 3/1998 |
| WO | WO 2014/103811 A1 | 7/2014 |

OTHER PUBLICATIONS

Burwell Jr et al., "The Action of Some Strong Acids on Secondary Phenylpentanes", Journal of the American Chemical Society, vol. 77, May 20, 1955, pp. 2766-2771.
Eliel et al., "Racemization of Phenylalkanes in Presence of Lewis Acids", The Journal of Organic Chemistry, vol. 22, No. 3, Apr. 29, 1957, pp. 231-234.
Field et al., "o-Quinonoid Compounds. Part 14. 1,5-Acyl Shifts in Substituted Indenes: Migratory Aptitudes from Racemisation Rates", Journal of Chemical Society, Perkin Transactions 1, No. 9, 1978, pp. 1050-1058.
Field et al., "o-Quinonoid Compounds. Part 16. 1,5-Shift of Vinyl Groups in 1,3-Dimethylindenes; Product Studies and Migratory Aptitudes of Substituted Vinyl Groups", Journal of Chemcial Society, Perkins Transactions 1, 1980, pp. 714-721.
Kim et al., "Fast racemization and dynamic kinetic resolution of primary benzyl amines", Tetrahedron Letters vol. 51, 2010 (Published online Aug. 20, 2010), pp. 5581-5584.
Pietruszka et al., "Dynamic Enzymatic Kinetic Resolution of Methyl 2,3-Dihydro-1H-indene-1-carboxylate", European Journal of Organic Chemistry, 2009 (Published online Oct. 23, 2009), pp. 6217-6224.
First Office Action (including an English translation thereof) issued in the corresponding Chinese Patent Application No. 201380056175.8 on Nov. 10, 2015.

* cited by examiner

*Primary Examiner* — Shailendra Kumar
(74) *Attorney, Agent, or Firm* — Birch, Stewart, Kolasch & Birch, LLP

(57) ABSTRACT

A method for producing a racemate of a compound represented by Formula (1), including bringing a transition metal catalyst into contact with an optically active form of the compound represented by Formula (1):

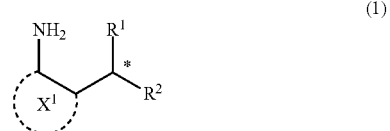

[in Formula (1),
a ring $X^1$ represents an aromatic ring;
$R^1$ represents a $C_{1-6}$ alkyl group, a $C_{3-8}$ cycloalkyl group, or a $C_{1-6}$ halo-alkyl group;
$R^2$ is a group different from $R^1$ and represents a $C_{1-6}$ alkyl group, a $C_{3-8}$ cycloalkyl group, or a $C_{1-6}$ halo-alkyl group, or $R^2$ and the ring $X^1$ are bonded to each other to form a ring;
a hydrogen atom(s) of the ring $X^1$ is optionally replaced with a $C_{1-6}$ alkyl group, a $C_{1-6}$ halo-alkyl group, a cyano group, a nitro group, a $C_{1-6}$ alkoxy group, or a halogen atom; and
* represents an asymmetric carbon atom].

11 Claims, No Drawings

METHOD FOR PRODUCING RACEMATE OF COMPOUND

This application is 371 of PCT/JP2013/079655, filed on Oct. 28, 2013.

TECHNICAL FIELD

The present invention relates to a method for producing a racemate from an optically active form of a compound.

BACKGROUND ART

Patent Literature 1 describes (3R)-1,1,3-trimethyl-4-aminoindane as an intermediate for use in producing agricultural chemicals, etc.

Non-Patent Literature 1 describes a method for racemizing an optically active form of 2-phenylbutane by bringing an optically active form of 2-phenylbutane into contact with aluminum chloride.

However, a method for racemizing an optically active form of (3R)-1,1,3-trimethyl-4-aminoindane, etc. is not known.

CITATION LIST

Patent Literature

[Patent Literature 1] Japanese Unexamined Patent Application Publication No. 1-211568

Non-Patent Literature

[Non-Patent Literature 1] R. L. Burwell, J R; J. Am. Chem. Soc., 77, 2766 (1955), E. L. Eliel; J. Org. Chem., 22,231 (1957)

SUMMARY OF INVENTION

Technical Problem

There is a demand for a method for efficiently producing a racemate from an optically active form of a compound of (3R)-1,1,3-trimethyl-4-aminoindane, etc.

Solution to Problem

The present invention includes the following aspects of the invention.

[1] A method for producing a racemate of a compound represented by Formula (1), comprising bringing a transition metal catalyst into contact with an optically active form of the compound represented by Formula (1):

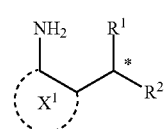

(1)

[in Formula (1),
a ring $X^1$ represents an aromatic ring;
$R^1$ represents a $C_{1-6}$ alkyl group, a $C_{3-8}$ cycloalkyl group, or a $C_{1-6}$ halo-alkyl group;
$R^2$ is a group different from $R^1$ and represents a $C_{1-6}$ alkyl group, a $C_{3-8}$ cycloalkyl group, or a $C_{1-6}$ halo-alkyl group, or $R^2$ and the ring $X^1$ are bonded to each other to form a ring;
a hydrogen atom of the ring $X^1$ is optionally replaced with a $C_{1-6}$ alkyl group, a $C_{1-6}$ halo-alkyl group, a cyano group, a nitro group, a $C_{1-6}$ alkoxy group, or a halogen atom; and
* represents an asymmetric carbon atom].

[2] The production method as described in [1], in which the compound represented by Formula (1) is a compound represented by Formula (1a):

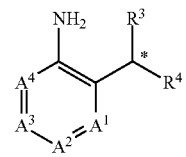

(1a)

[in Formula (1a),
$A^1, A^2, A^3$, and $A^4$ each independently represent —N= or —C($R^a$)=, and $R^a$ represents a hydrogen atom, a $C_{1-6}$ alkyl group, a $C_{1-6}$ halo-alkyl group, a cyano group, a nitro group, a $C_{1-6}$ alkoxy group, or a halogen atom;
$R^3$ represents a $C_{1-6}$ alkyl group, a $C_{3-8}$ cycloalkyl group, or a $C_{1-6}$ halo-alkyl group;
$R^4$ is a group different from $R^3$ and represents a $C_{1-6}$ alkyl group, a $C_{3-8}$ cycloalkyl group, or a $C_{1-6}$ halo-alkyl group, or when $A^1$ represents —C($R^a$)=, $R^4$ and $R^a$ are optionally bonded to each other to form a divalent hydrocarbon group, a hydrogen atom(s) of the hydrocarbon group is optionally replaced with a halogen atom, and —$CH_2$— of the hydrocarbon group is optionally replaced with —O—;
two $R^a$'s of the adjacent —C($R^a$)='s are optionally bonded to each other to form a benzene ring with a carbon atom to which each of them is bonded, and a hydrogen atom(s) of the benzene ring is optionally replaced with a $C_{1-6}$ alkyl group or a halogen atom; and
* represents an asymmetric carbon atom].

[3] The production method as described in [2], in which $A^1$, $A^2$, $A^3$, and $A^4$ are —C($R^a$)=.

[4] The production method as described in [2] or [3], in which $A^1$ is —C($R^a$)=, and $R^a$ and $R^4$ are bonded to each other to form a divalent hydrocarbon group.

[5] The production method as described in any one of [2] to [4], in which the compound represented by Formula (1a) is a compound represented by Formula (2):

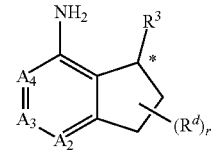

(2)

[in Formula (2),
$A^2, A^3$, and $A^4$ each independently represent —N= or —C($R^a$)=, $R^a$ represents a hydrogen atom, a $C_{1-6}$ alkyl group, a $C_{1-6}$ halo-alkyl group, or a halogen atom, and $R^3$ represents a $C_{1-6}$ alkyl group;
$R^d$ represents a $C_{1-6}$ alkyl group, or a $C_{1-6}$ halo-alkyl group, r represents an integer of 0 to 4, and when r is an integer of 2 or more, a plurality of $R^d$'s are optionally the same or different; and
* represents an asymmetric carbon atom].

[6] The production method as described in any one of [2] to [5], in which $R^3$ is a $C_{1-6}$ alkyl group.

[7] The production method as described in any one of [1] to [6], in which the compound represented by Formula (1) is a compound represented by Formula (3):

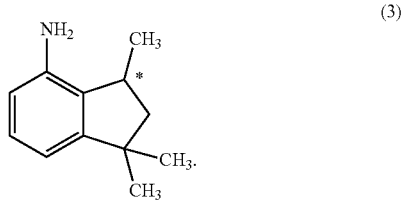

[8] The production method as described in any one of [1] to [7], in which the transition metal catalyst is a hydrogen absorbing transition metal catalyst having absorbed hydrogen therein.

[9] The production method as described in any one of [1] to [8], in which the transition metal catalyst is a palladium catalyst.

[10] The production method as described in [9], in which the palladium catalyst is a palladium-carbon catalyst.

[11] A method for racemizing a compound represented by Formula (1), including bringing a transition metal catalyst into contact with an optically active form of the compound represented by Formula (1):

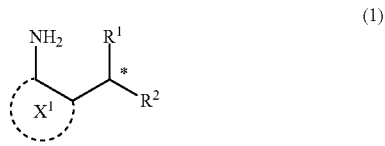

[in Formula (1), a ring $X^1$ represents an aromatic ring;

$R^1$ represents a $C_{1-6}$ alkyl group, a $C_{3-8}$ cycloalkyl group, or a $C_{1-6}$ halo-alkyl group;

$R^2$ is a group different from $R^1$ and represents a $C_{1-6}$ alkyl group, a $C_{3-8}$ cycloalkyl group, or a $C_{1-6}$ halo-alkyl group, or $R^2$ and the ring $X^1$ are bonded to each other to form a ring;

a hydrogen atom(s) of the ring $X^1$ is optionally replaced with a $C_{1-6}$ alkyl group, a $C_{1-6}$ halo-alkyl group, a cyano group, a nitro group, a $C_{1-6}$ alkoxy group, or a halogen atom; and

* represents an asymmetric carbon atom].

Advantageous Effects of Invention

According to the present invention, a racemate can be efficiently produced from an optically active form of the compound represented by Formula (1).

DESCRIPTION OF EMBODIMENTS

First, the compound represented by Formula (1) will be described.

The $C_{1-6}$ alkyl group represents an alkyl group having 1 to 6 carbon atoms and includes linear and branched chain alkyl groups. Examples of the $C_{1-6}$ alkyl group include a methyl group, an ethyl group, a propyl group, an isopropyl group, a butyl group, an isobutyl group, a sec-butyl group, a tert-butyl group, a pentyl group, a sec-pentyl group, an isopentyl group, and a neopentyl group, and preferred are a methyl group, an ethyl group, a propyl group, and an isopropyl group.

The $C_{3-8}$ cycloalkyl group represents a cyclic alkyl group having 3 to 8 carbon atoms, and examples of the $C_{1-8}$ cycloalkyl group include a cyclopropyl group, a 2,2-dimethylcyclopropyl group, a cyclobutyl group, a cyclopentyl group, a cyclohexyl group, a cycloheptyl group, and a cyclooctyl group, and preferred are a cyclopropyl group, a cyclopentyl group, and a cyclohexyl group.

The $C_{1-6}$ halo-alkyl group represents an alkyl group having 1 to 6 carbon atoms in which at least one of the hydrogen atom(s) is replaced with a halogen atom, and examples of the $C_{1-6}$ halo-alkyl group include a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a chlorofluoromethyl group, a dichlorofluoromethyl group, a fluoroethyl group, a chloroethyl group, a 1-chloro-1-fluoroethyl group, and a 1-chloro-2-fluoroethyl group, and preferred are a trifluoromethyl group and a difluoromethyl group.

The $C_{1-6}$ alkoxy group represents an alkoxy group having 1 to 6 carbon atoms, and examples of the $C_{1-6}$ alkoxy group include a methoxy group, an ethoxy group, a propoxy group, an isopropoxy group, a butoxy group, an isobutoxy group, a sec-butoxy group, and a tert-butoxy group, and preferably a methoxy group.

Examples of the halogen atom include a fluorine atom, a chlorine atom, a bromine atom, and an iodine atom.

The aromatic ring includes a homocycle and a heterocycle, and examples thereof include the following rings, and preferred are 5- and 6-membered rings.

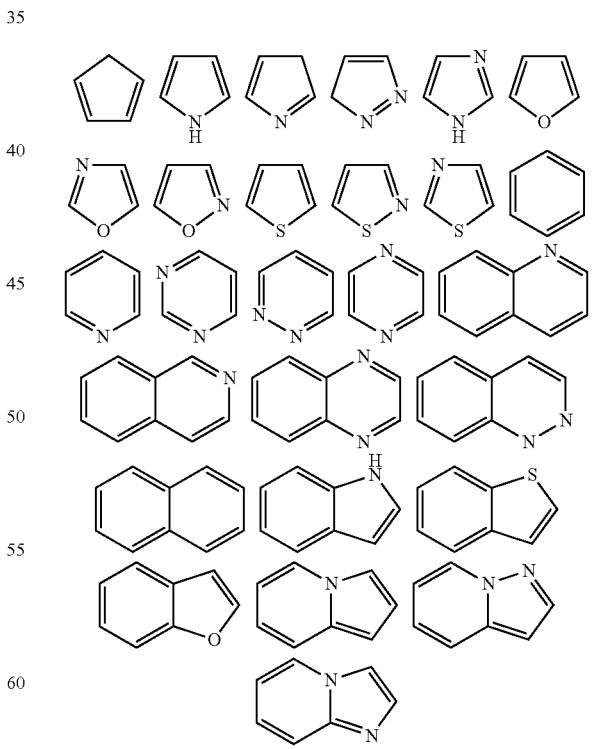

Examples of the ring formed by the mutual bonding of $R^2$ and the ring $X^1$ include the following rings, and preferred are 5- and 6-membered rings.

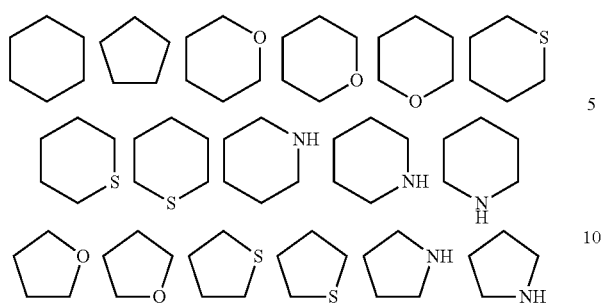

Among the compounds represented by Formula (1), a compound represented by Formula (1a) and a compound represented by Formula (1b) are preferred.

First, explanation will be made to Formula (1a).

Examples of the $C_{1-6}$ alkyl group, the $C_{3-8}$ cycloalkyl group, the $C_{1-6}$ halo-alkyl group, the $C_{1-6}$ alkoxy group, and the halogen atom in the compound represented by Formula (1a) include the same groups as in the compound represented by Formula (1), respectively.

Examples of the divalent hydrocarbon group formed by the mutual bonding of $R^4$ and $R^a$ include alkanediyl groups having 2 to 9 carbon atoms, such as an ethylene group, a propanediyl group, a 2-methyl-propane-1,2-diyl group, a butane-1,2-diyl group, a butanediyl group, a hexanediyl group, a heptanediyl group, an octanediyl group, and a nonanediyl group.

As the divalent hydrocarbon group formed by the mutual bonding of $R^4$ and $R^a$ and having —O— group in place of its —CH$_2$— group include —CH$_2$—O—CH$_2$— and —CH$_2$—CH$_2$—O—.

Among the compounds represented by Formula (1a) in which $R^3$ is a methyl group; a compound in which $A^1$, $A^2$, $A^3$, and $A^4$ are —C($R^a$)=; and a compound in which $A^1$ is —C($R^a$)=, and a compound in which $R^4$ and $R^a$ may be bonded to each other to form a divalent hydrocarbon group are preferred, and the compound represented by Formula (2) is more preferred.

Examples of the $C_{1-6}$ alkyl group, the $C_{1-6}$ halo-alkyl group, or the halogen atom in the compound represented by Formula (2) include the same groups as in the compound represented by Formula (1) and the compound represented by Formula (1a).

Next, explanation will be made to Formula (1b).

Examples of the $C_{1-6}$ alkyl group, the $C_{3-8}$ cycloalkyl group, the $C_{1-6}$ halo-alkyl group, the $C_{1-6}$ alkoxy group, and the halogen atom in the compound represented by Formula (1b) include the same groups as in the compound represented by Formula (1).

Examples of the divalent hydrocarbon group formed by the mutual bonding of $R^6$ and either $R^b$ or $R^c$ in the compound represented by Formula (1b) include the same groups as in the compound represented by Formula (1a).

Hereinafter, examples of the compounds represented by Formula (1) are specifically illustrated.

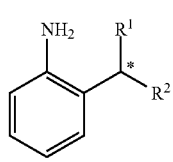
(1-1)

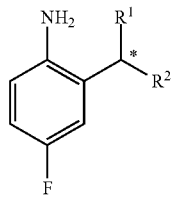
(1-2)

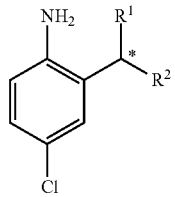
(1-3)

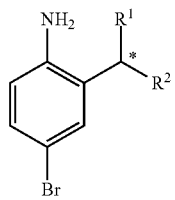
(1-4)

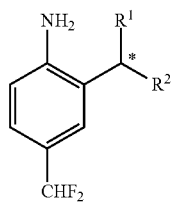
(1-5)

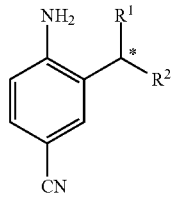
(1-6)

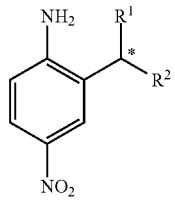
(1-7)

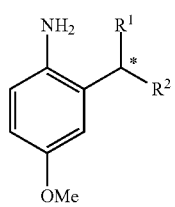
(1-8)

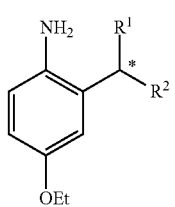 (1-9)
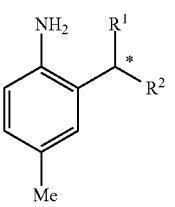 (1-10)
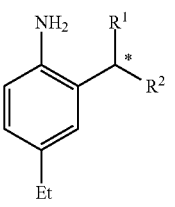 (1-11)
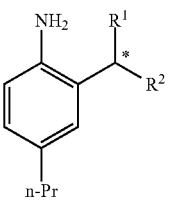 (1-12)
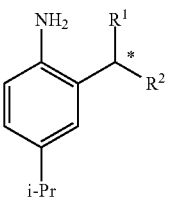 (1-13)
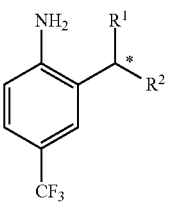 (1-14)
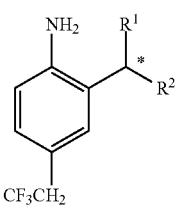 (1-15)
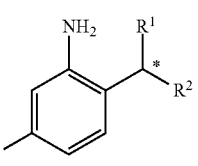 (1-16)
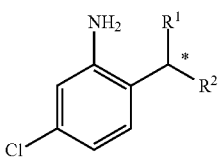 (1-17)
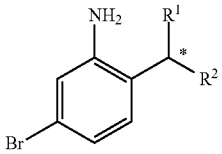 (1-18)
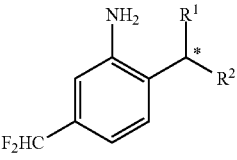 (1-19)
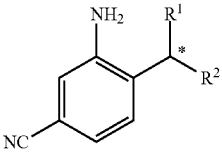 (1-20)
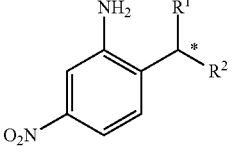 (1-21)
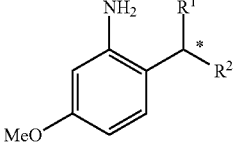 (1-22)
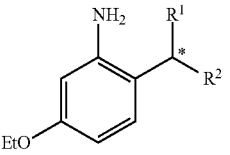 (1-23)
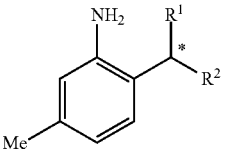 (1-24)
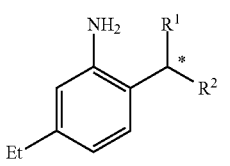 (1-25)

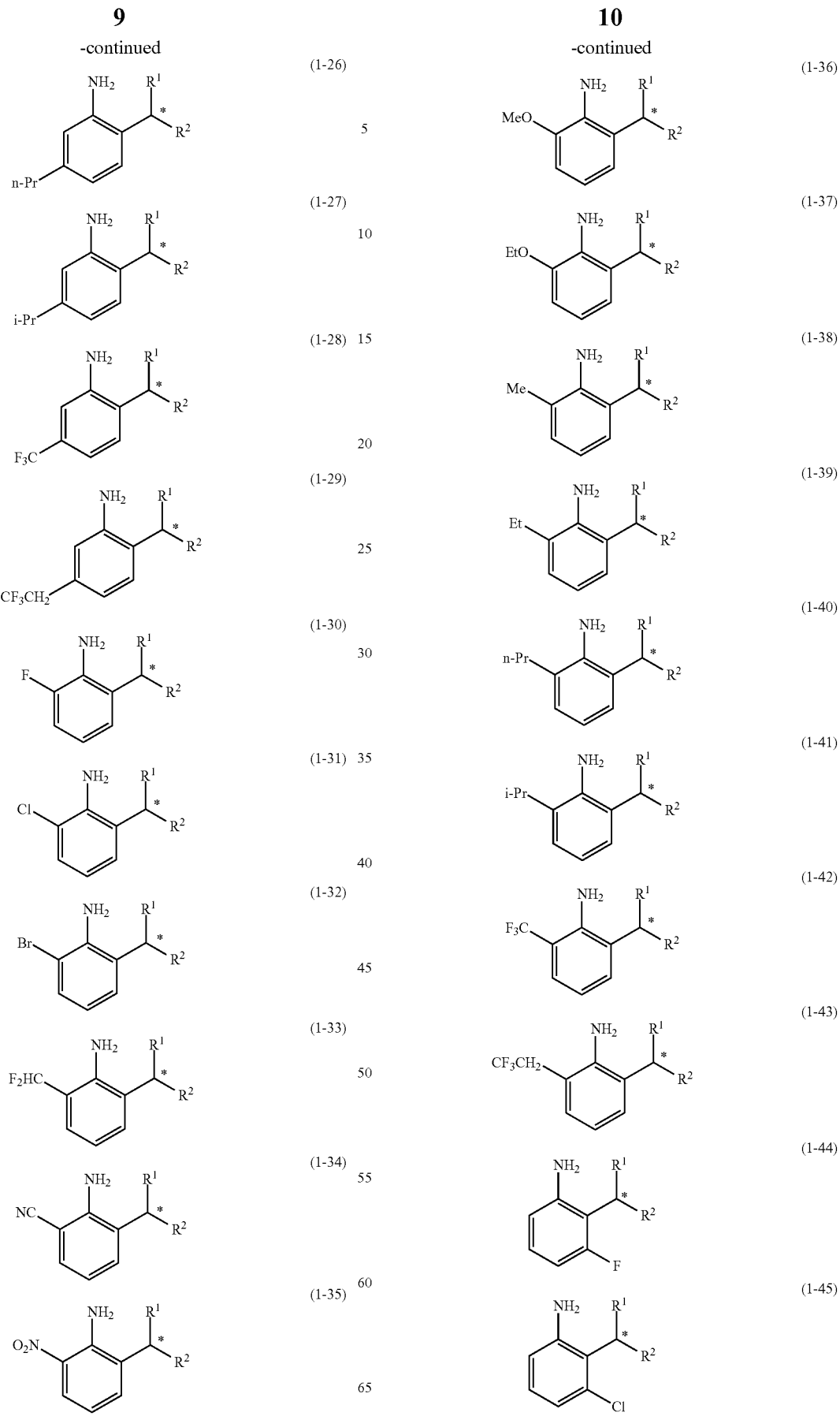

-continued
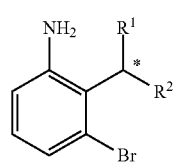 (1-46)
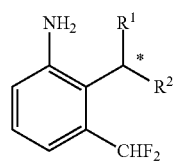 (1-47)
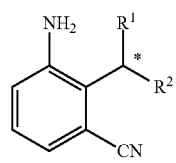 (1-48)
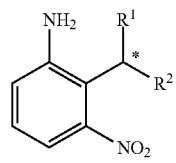 (1-49)
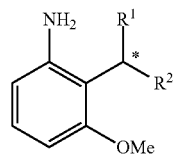 (1-50)
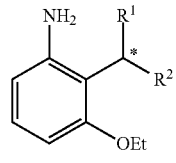 (1-51)
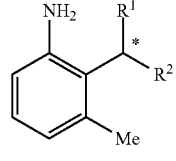 (1-52)
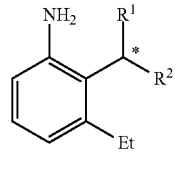 (1-53)
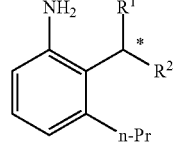 (1-54)
-continued
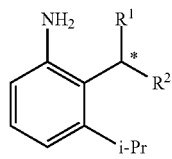 (1-55)
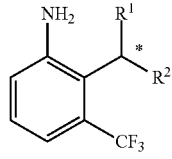 (1-56)
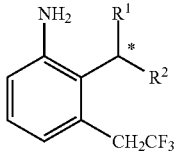 (1-57)
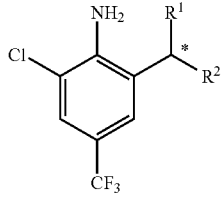 (1-58)
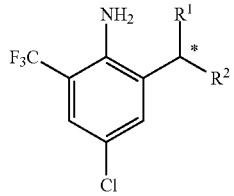 (1-59)
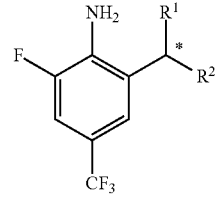 (1-60)
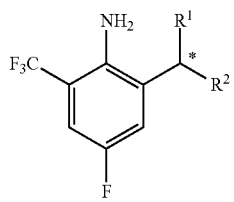 (1-61)
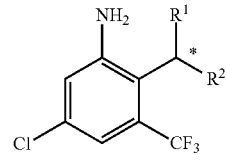 (1-62)

| | |
|---|---|
| (1-63) | (1-72) |
| (1-64) | (1-73) |
| (1-65) | (1-74) |
| (1-66) | (1-75) |
| (1-67) | (1-76) |
| (1-68) | (1-77) |
| (1-69) | (1-78) |
| (1-70) | |
| (1-71) | |

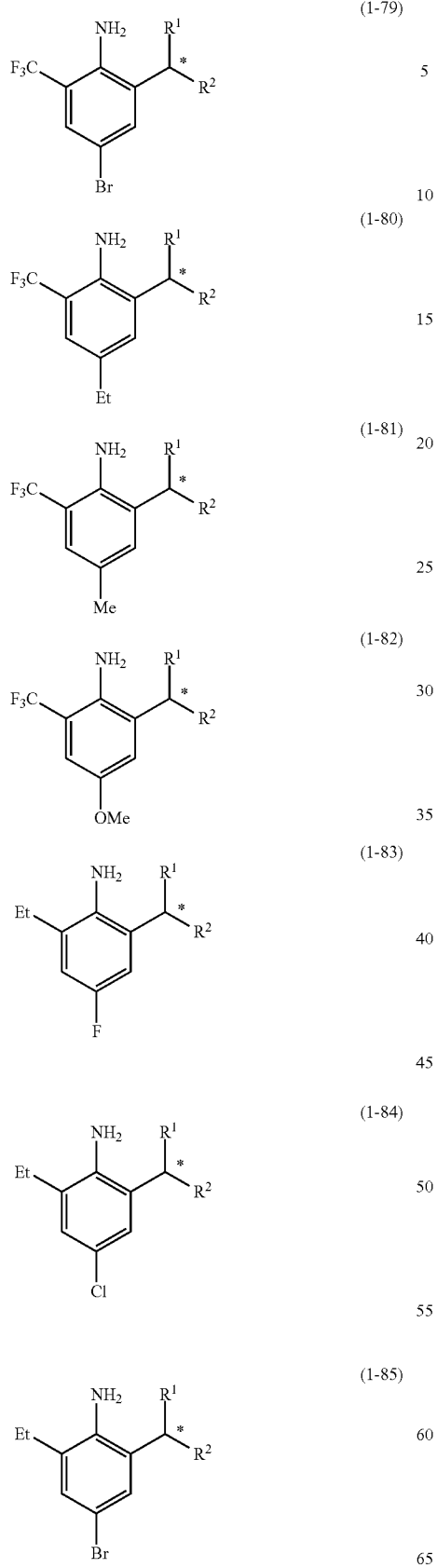

| | |
|---|---|
| (1-93) | (1-100) |
| (1-94) | (1-101) |
| (1-95) | (1-102) |
| (1-96) | (1-103) |
| (1-97) | (1-104) |
| (1-98) | (1-105) |
| (1-99) | (1-106) |
| | (1-107) |

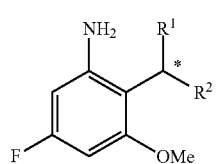 (1-108)
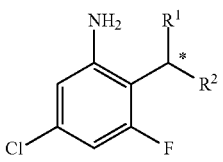 (1-109)
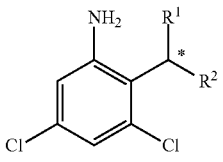 (1-110)
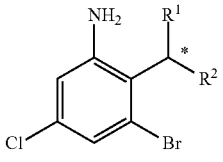 (1-111)
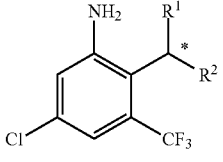 (1-112)
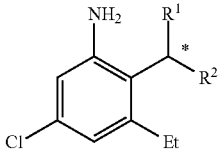 (1-113)
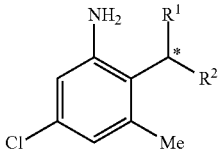 (1-114)
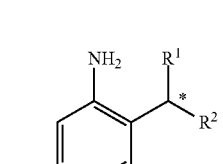 (1-115)
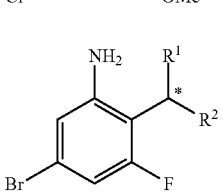 (1-116)
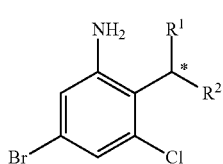 (1-117)
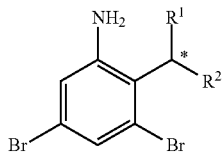 (1-118)
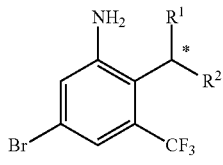 (1-119)
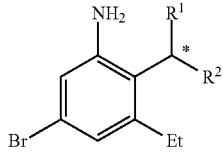 (1-120)
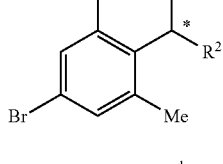 (1-121)
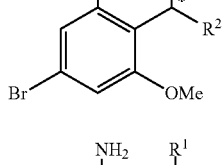 (1-122)
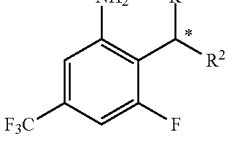 (1-123)
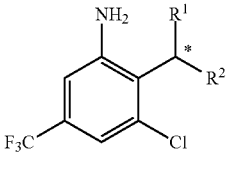 (1-124)
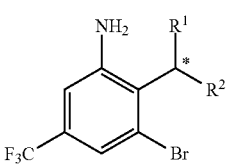 (1-125)

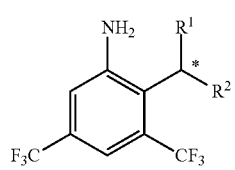
(1-126)
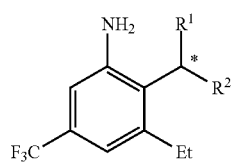
(1-127)
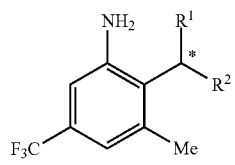
(1-128)
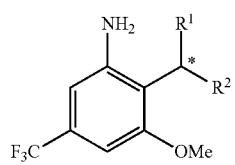
(1-129)
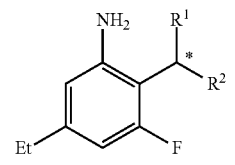
(1-130)
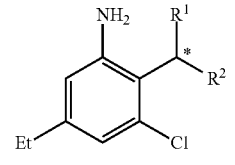
(1-131)
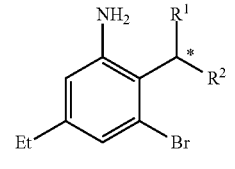
(1-132)
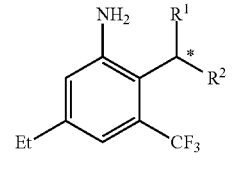
(1-133)
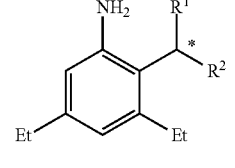
(1-134)
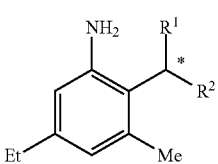
(1-135)
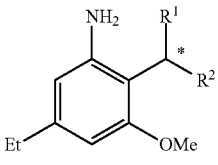
(1-136)
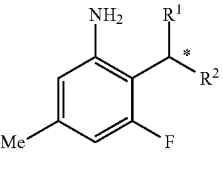
(1-137)
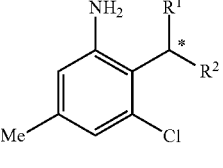
(1-138)
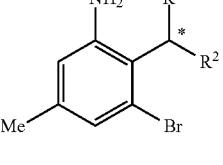
(1-139)
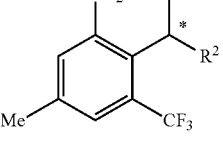
(1-140)
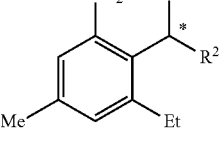
(1-141)
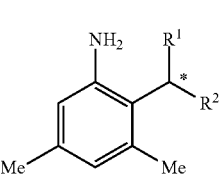
(1-142)
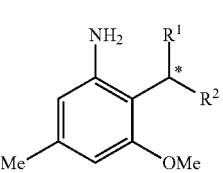
(1-143)

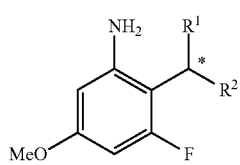 (1-144)
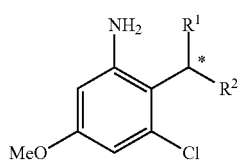 (1-145)
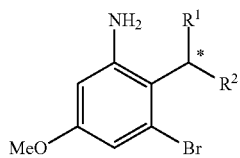 (1-146)
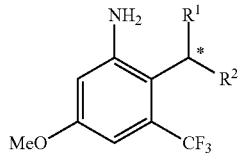 (1-147)
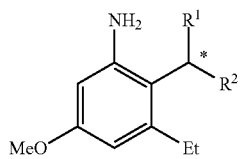 (1-148)
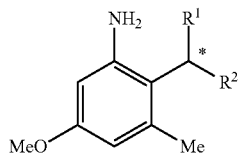 (1-149)
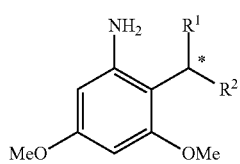 (1-150)
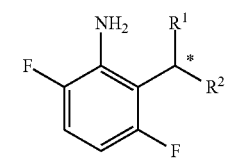 (1-151)
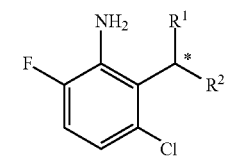 (1-152)
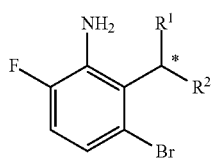 (1-153)
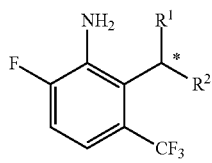 (1-154)
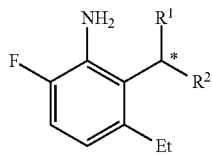 (1-155)
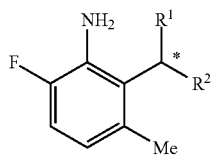 (1-156)
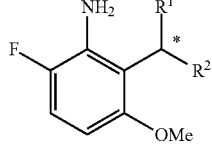 (1-157)
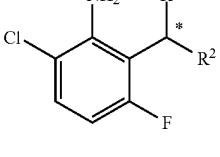 (1-158)
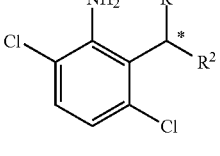 (1-159)
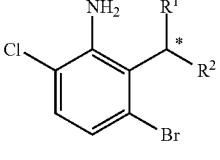 (1-160)
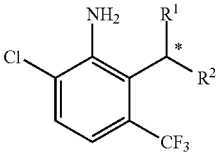 (1-161)

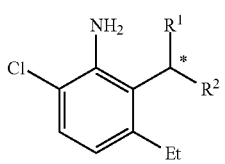 (1-162)
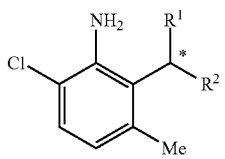 (1-163)
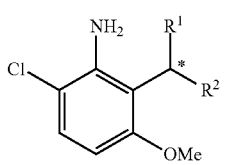 (1-164)
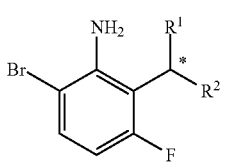 (1-165)
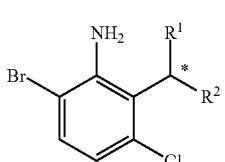 (1-166)
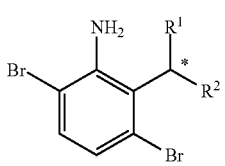 (1-167)
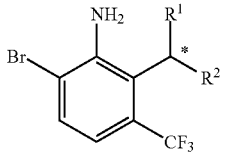 (1-168)
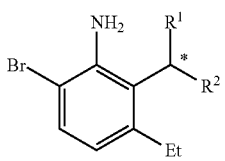 (1-169)
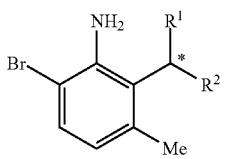 (1-170)
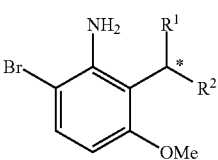 (1-171)
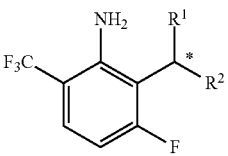 (1-172)
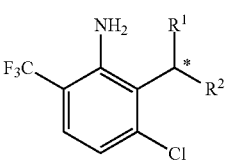 (1-173)
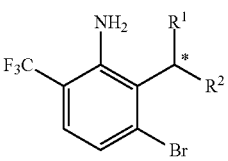 (1-174)
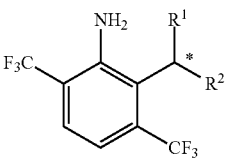 (1-175)
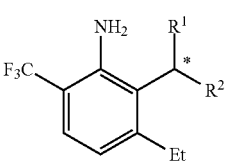 (1-176)
 (1-177)
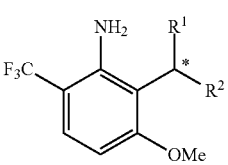 (1-178)
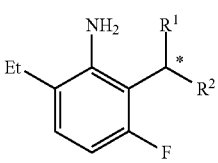 (1-179)

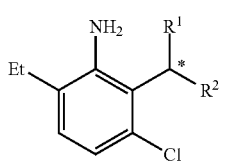
(1-180)
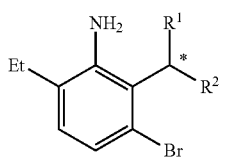
(1-181)
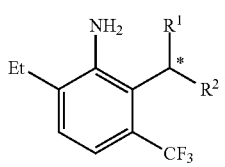
(1-182)
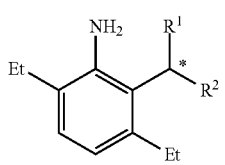
(1-183)
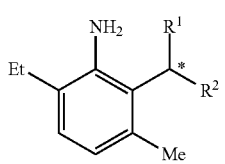
(1-184)
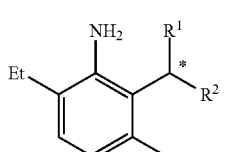
(1-185)
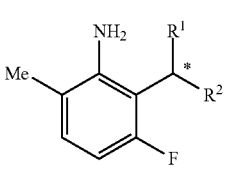
(1-186)
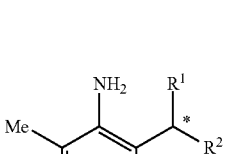
(1-187)
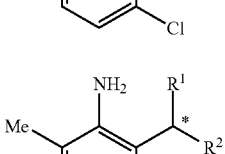
(1-188)
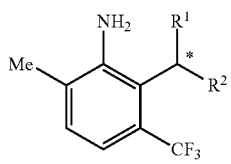
(1-189)
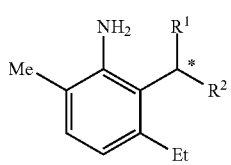
(1-190)
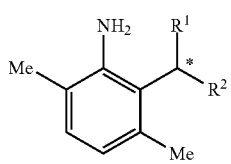
(1-191)
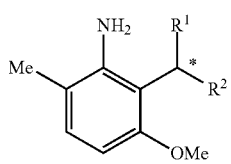
(1-192)
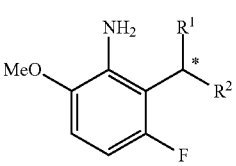
(1-193)
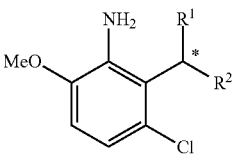
(1-194)
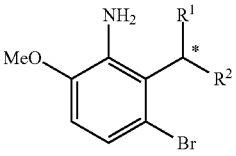
(1-195)
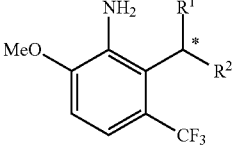
(1-196)
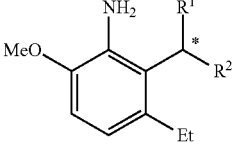
(1-197)

-continued
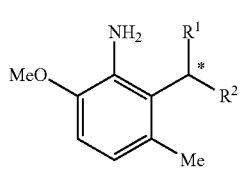 (1-198)
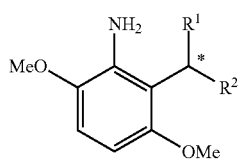 (1-199)
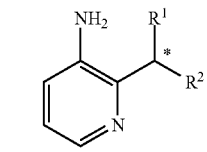 (1-200)
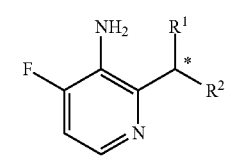 (1-201)
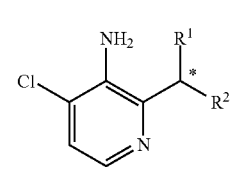 (1-202)
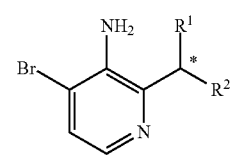 (1-203)
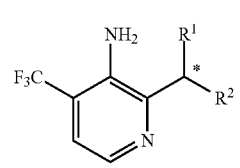 (1-204)
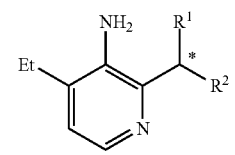 (1-205)
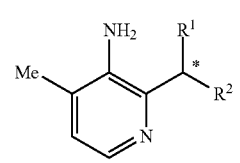 (1-206)
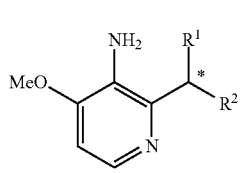 (1-207)
-continued
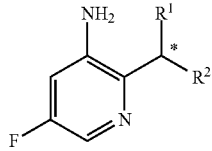 (1-208)
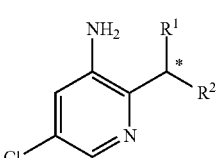 (1-209)
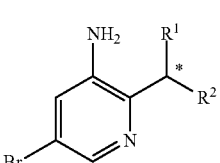 (1-210)
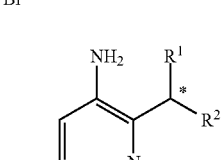 (1-211)
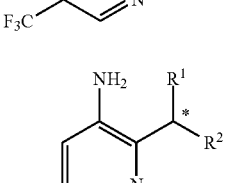 (1-212)
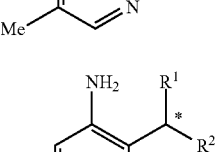 (1-213)
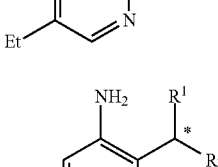 (1-214)
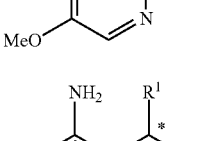 (1-215)
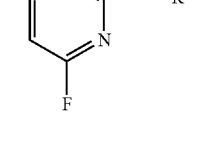 (1-216)

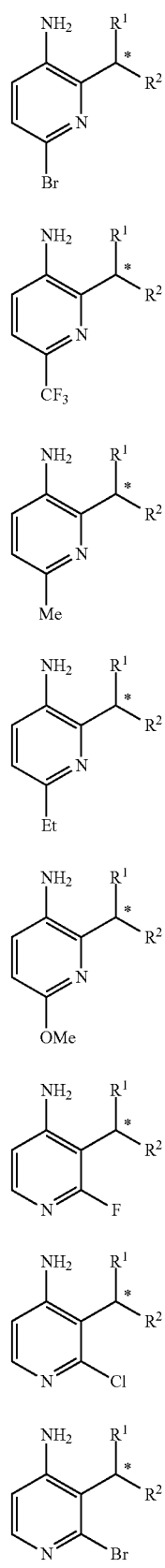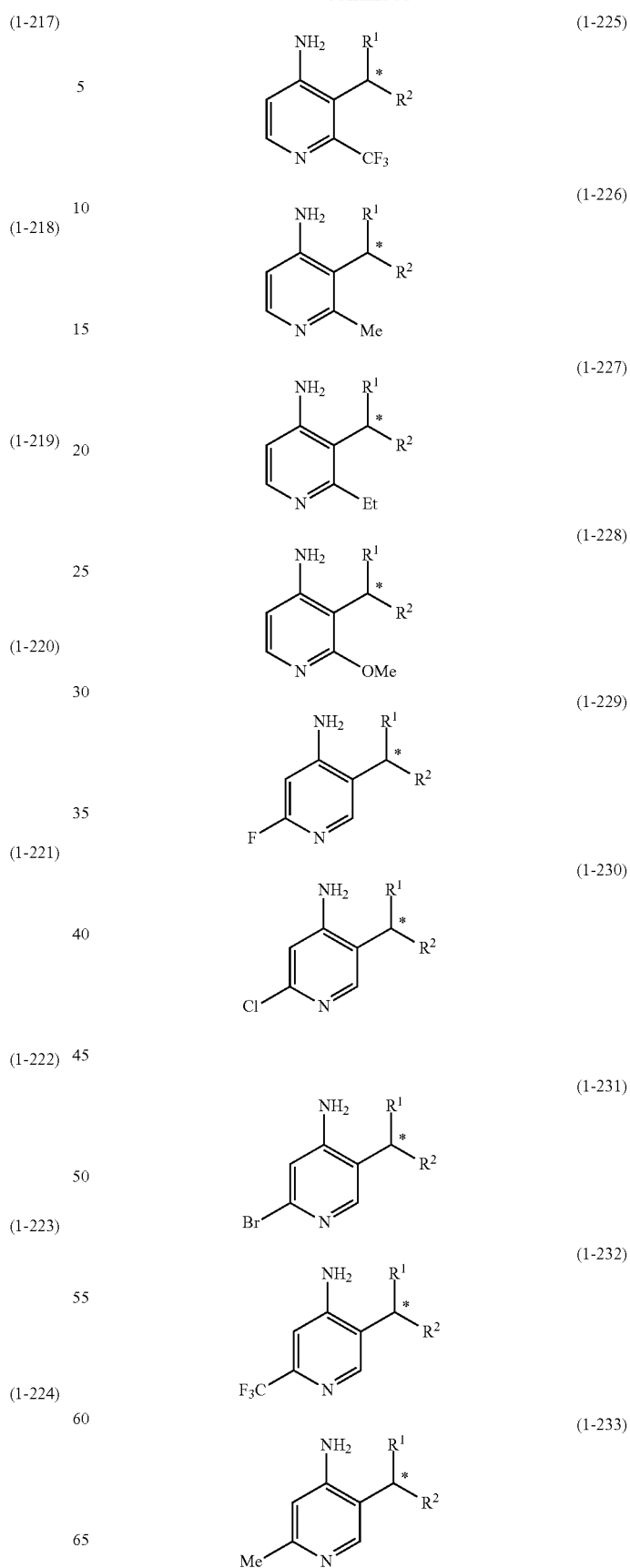

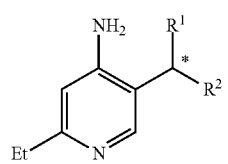 (1-234)
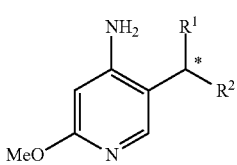 (1-235)
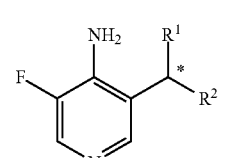 (1-236)
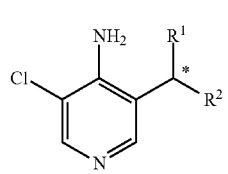 (1-237)
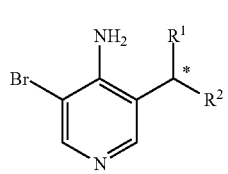 (1-238)
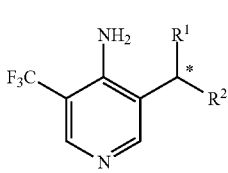 (1-239)
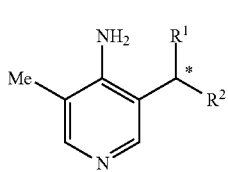 (1-240)
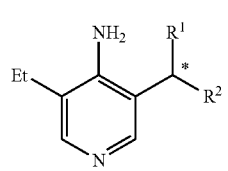 (1-241)
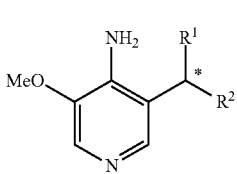 (1-242)
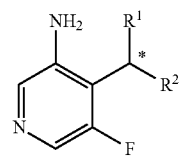 (1-243)
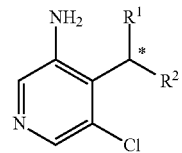 (1-244)
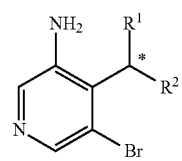 (1-245)
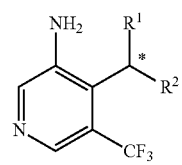 (1-246)
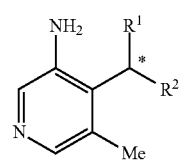 (1-247)
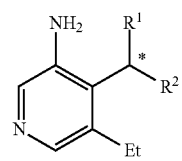 (1-248)
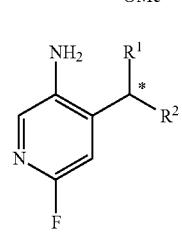 (1-249)
(1-250)
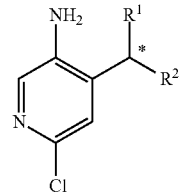 (1-251)

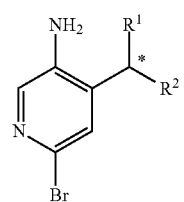 (1-252)
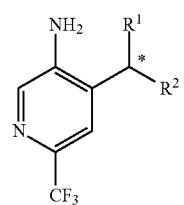 (1-253)
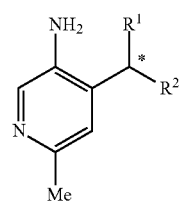 (1-254)
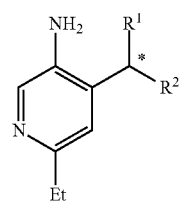 (1-255)
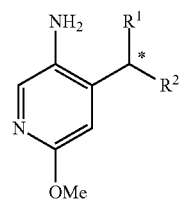 (1-256)
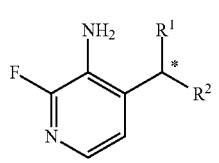 (1-257)
 (1-258)
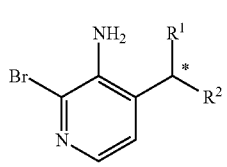 (1-259)
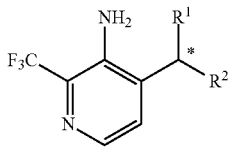 (1-260)
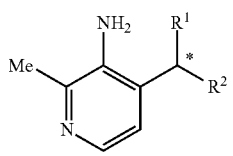 (1-261)
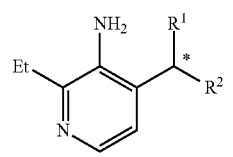 (1-262)
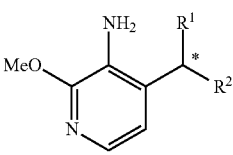 (1-263)
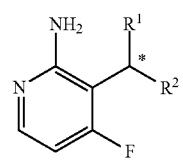 (1-264)
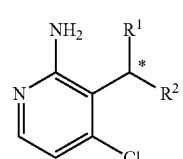 (1-265)
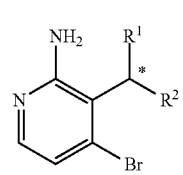 (1-266)
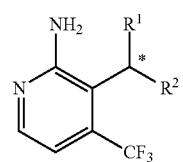 (1-267)
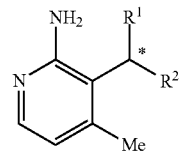 (1-268)
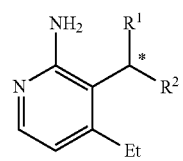 (1-269)

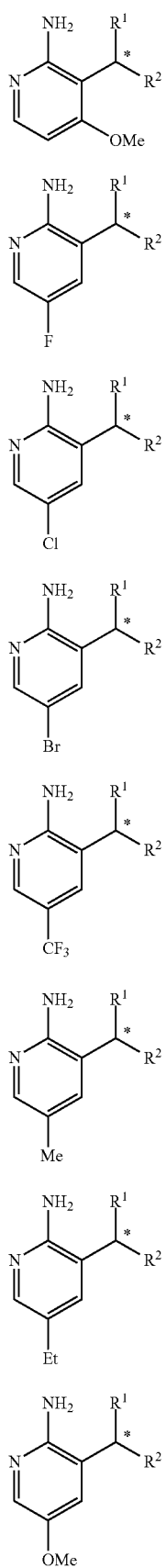
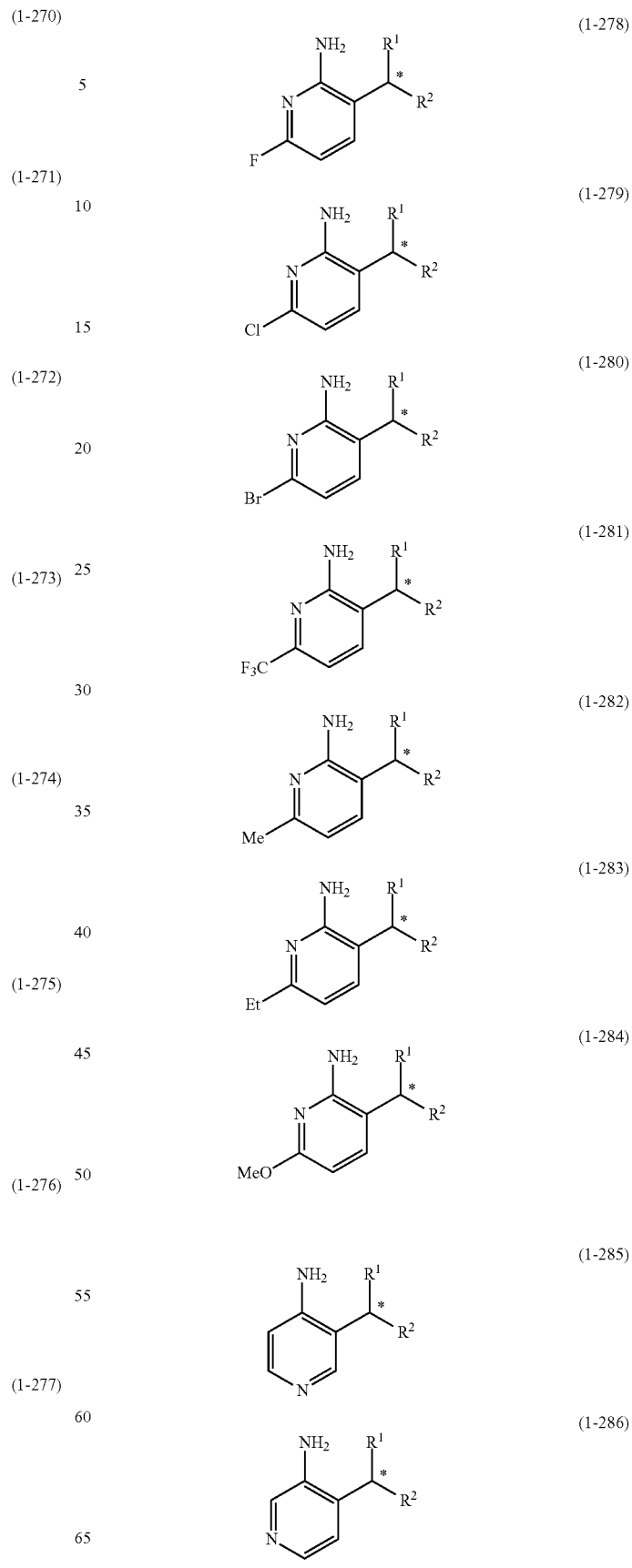

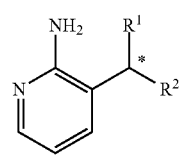 (1-287)
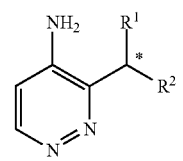 (1-288)
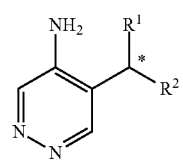 (1-289)
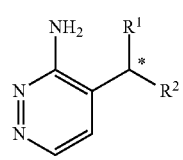 (1-290)
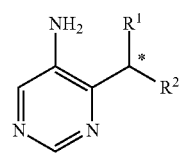 (1-291)
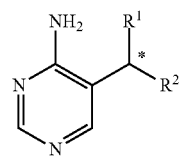 (1-292)
 (1-293)
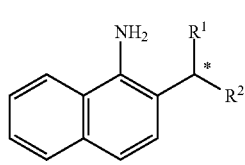 (1-294)
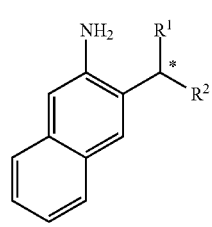 (1-295)
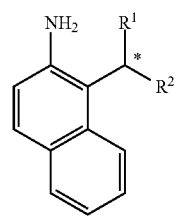 (1-296)
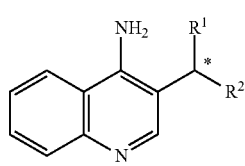 (1-297)
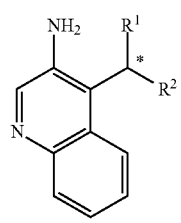 (1-298)
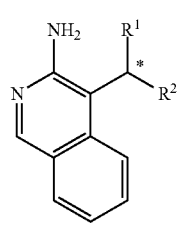 (1-299)
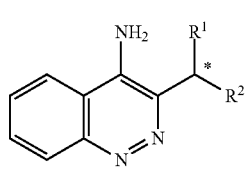 (1-300)
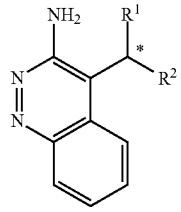 (1-301)
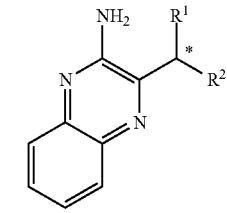 (1-302)
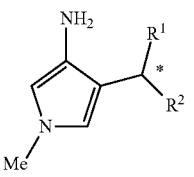 (1-303)

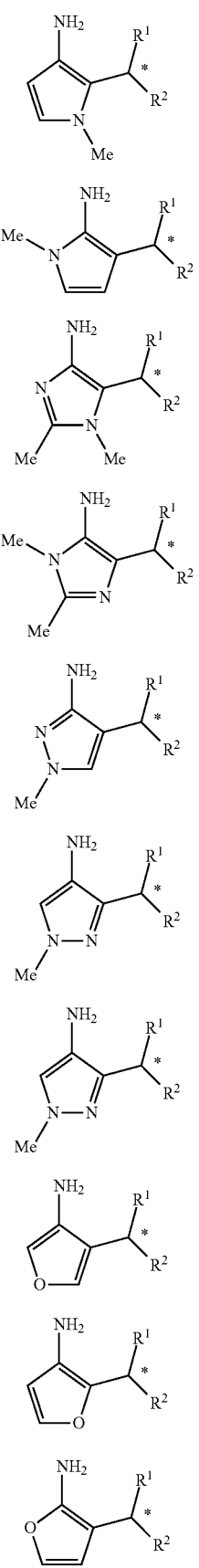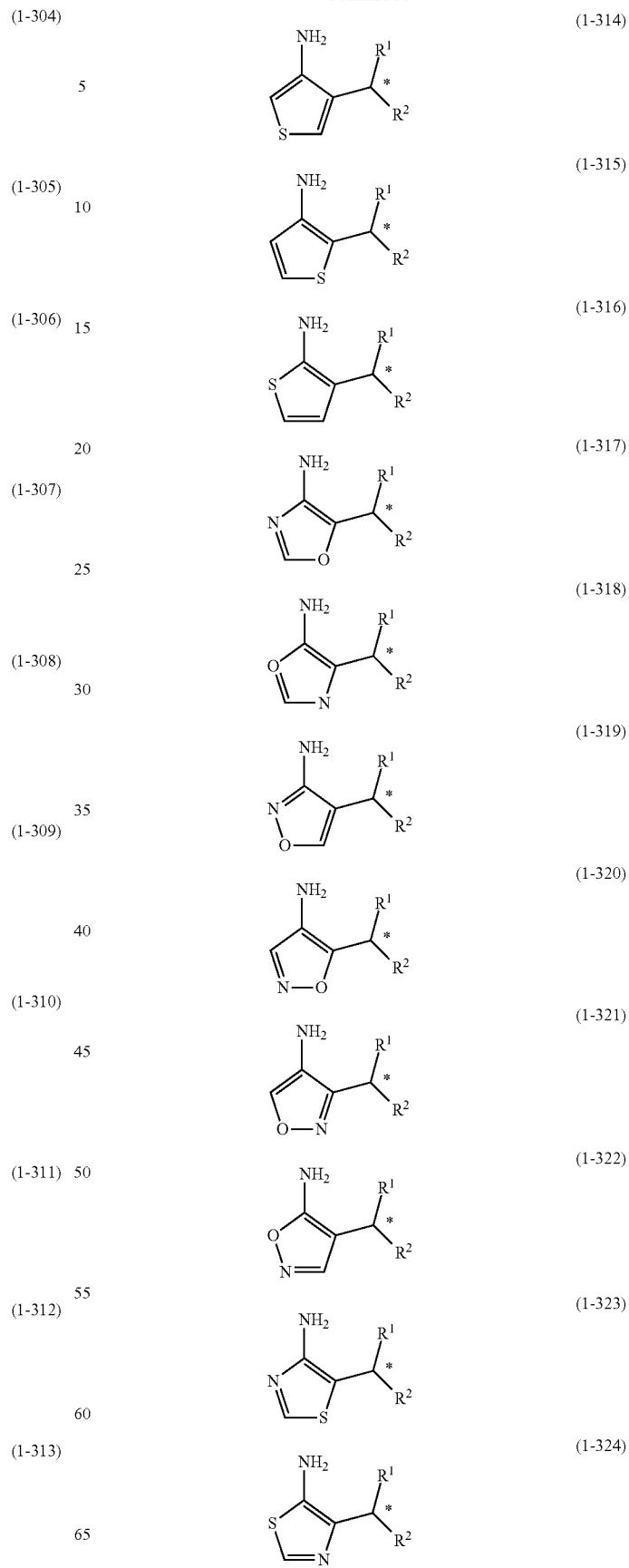

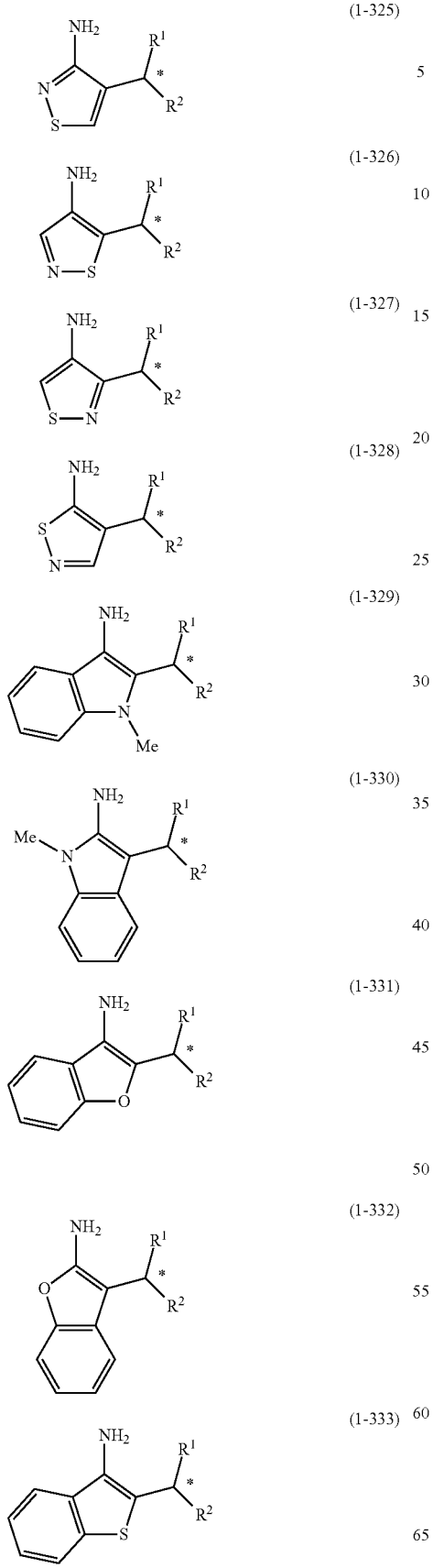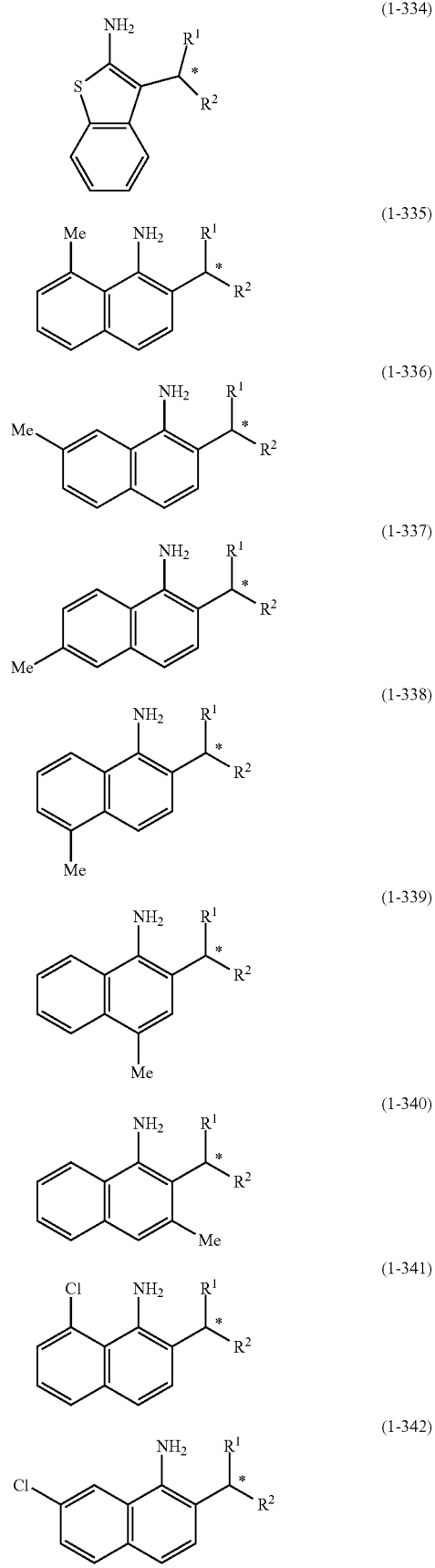

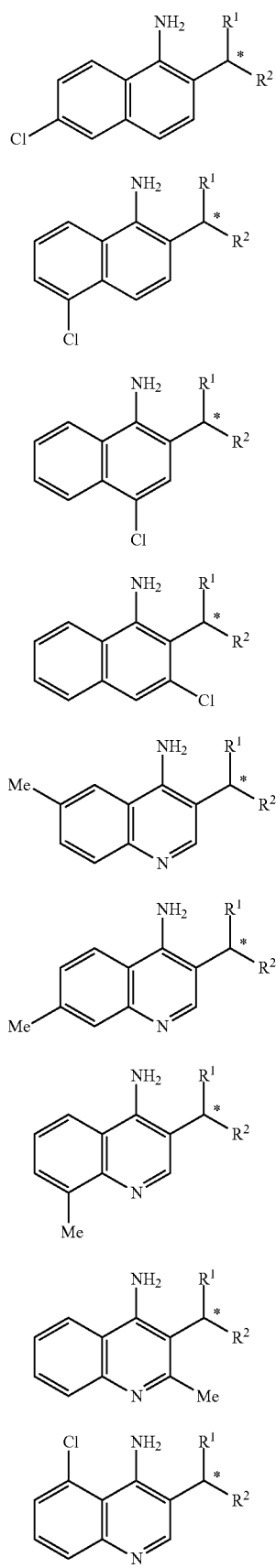
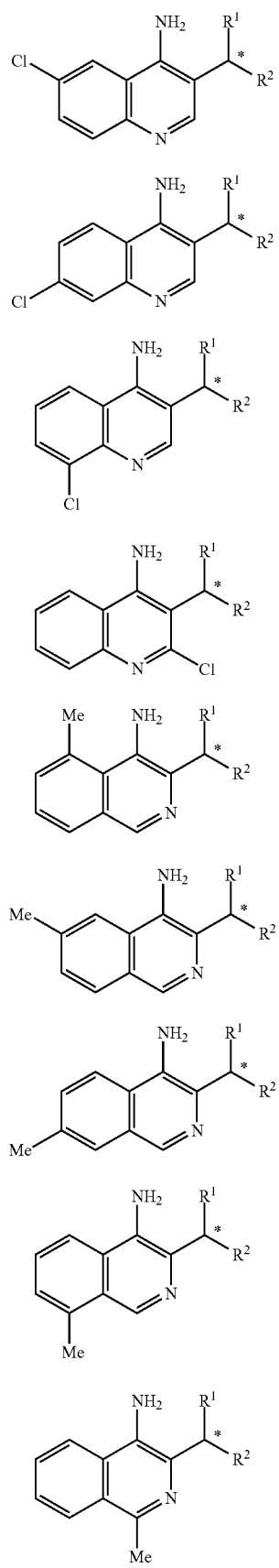

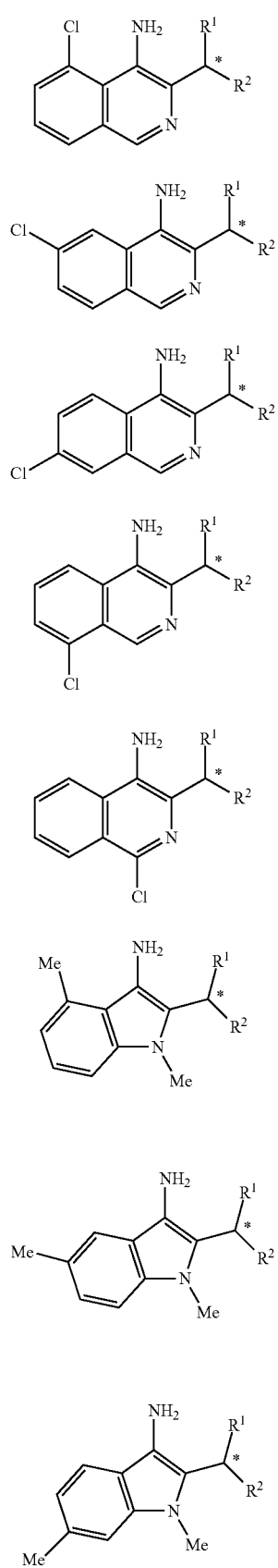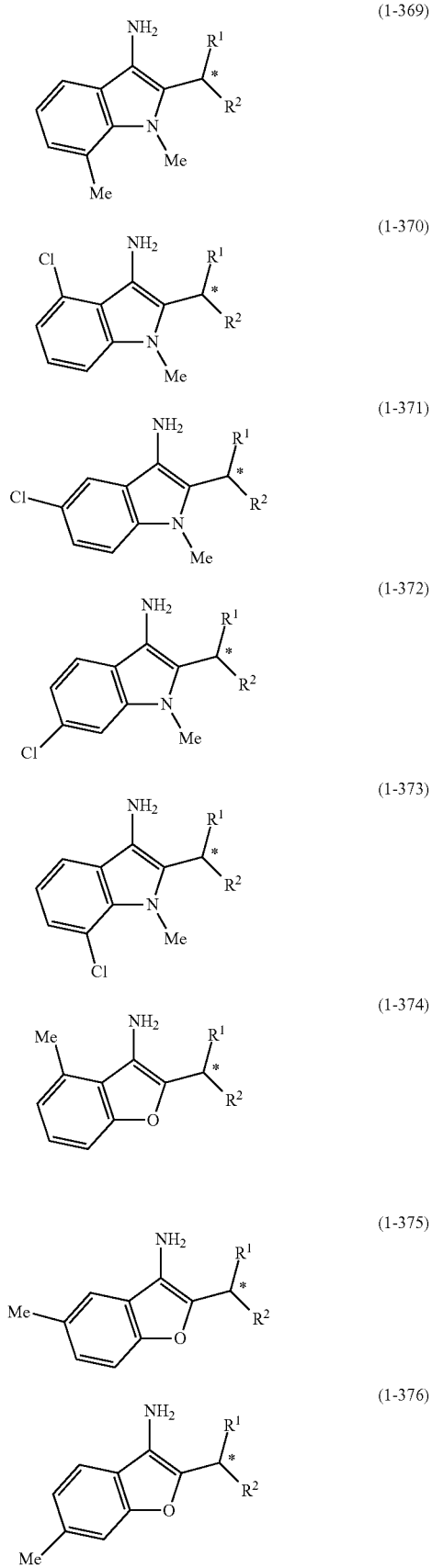

-continued

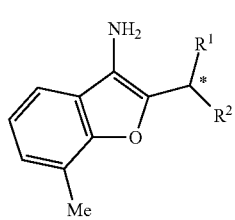
(1-377)

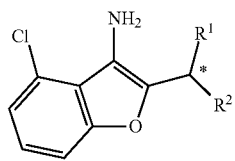
(1-378)

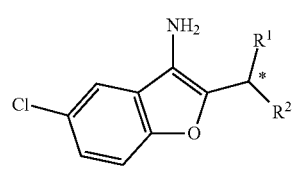
(1-379)

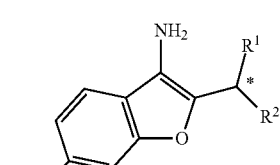
(1-380)

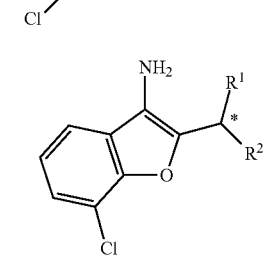
(1-381)

Examples of $R^1$ and $R^2$ in the compounds represented by Formulae (1-1) to (1-381) include the groups described in Tables below. For example, the compounds represented by Formula (A-1) refer to the compounds represented by Formulae (1-1) to (1-381), in which $R^1$ is a methyl group and $R^2$ is an ethyl group.

TABLE 1

| Formula | $R^1$ | $R^2$ |
|---|---|---|
| A-1 | Methyl group | Ethyl group |
| A-2 | Methyl group | Propyl group |
| A-3 | Methyl group | Isopropyl group |
| A-4 | Methyl group | Butyl group |
| A-5 | Methyl group | Isobutyl group |
| A-6 | Methyl group | sec-Isobutyl group |
| A-7 | Methyl group | tert-Isobutyl group |
| A-8 | Ethyl group | Propyl group |
| A-9 | Ethyl group | Isopropyl group |
| A-10 | Ethyl group | Butyl group |
| A-11 | Ethyl group | Isobutyl group |
| A-12 | Ethyl group | sec-Isobutyl group |
| A-13 | Ethyl group | tert-Isobutyl group |
| A-14 | Propyl group | Isopropyl group |
| A-15 | Propyl group | Butyl group |
| A-16 | Propyl group | Isobutyl group |
| A-17 | Propyl group | sec-Isobutyl group |
| A-18 | Propyl group | tert-Isobutyl group |

TABLE 1-continued

| Formula | $R^1$ | $R^2$ |
|---|---|---|
| A-19 | Isopropyl group | Butyl group |
| A-20 | Isopropyl group | Isobutyl group |

TABLE 2

| Formula | $R^1$ | $R^2$ |
|---|---|---|
| A-21 | Isopropyl group | sec-Isobutyl group |
| A-22 | Isopropyl group | tert-Isobutyl group |
| A-23 | Butyl group | Isobutyl group |
| A-24 | Butyl group | sec-Isobutyl group |
| A-25 | Butyl group | tert-Isobutyl group |
| A-26 | Isobutyl group | sec-Isobutyl group |
| A-27 | Isobutyl group | tert-Isobutyl group |
| A-28 | sec-Isobutyl group | tert-Isobutyl group |
| A-29 | Methyl group | Cyclopropyl group |
| A-30 | Methyl group | Cyclopentyl group |
| A-31 | Methyl group | Cyclohexyl group |
| A-32 | Methyl group | Difluoromethyl group |
| A-33 | Methyl group | Trifluoromethyl group |
| A-34 | Ethyl group | Cyclopropyl group |
| A-35 | Ethyl group | Cyclopentyl group |
| A-36 | Ethyl group | Cyclohexyl group |
| A-37 | Ethyl group | Difluoromethyl group |
| A-38 | Ethyl group | Trifluoromethyl group |
| A-39 | Propyl group | Cyclopropyl group |
| A-40 | Propyl group | Cyclopentyl group |

TABLE 3

| Formula | $R^1$ | $R^2$ |
|---|---|---|
| A-41 | Propyl group | Cyclohexyl group |
| A-42 | Propyl group | Difluoromethyl group |
| A-43 | Propyl group | Trifluoromethyl group |
| A-44 | Isopropyl group | Cyclopropyl group |
| A-45 | Isopropyl group | Cyclopentyl group |
| A-46 | Isopropyl group | Cyclohexyl group |
| A-47 | Isopropyl group | Difluoromethyl group |
| A-48 | Isopropyl group | Trifluoromethyl group |
| A-49 | Butyl group | Cyclopropyl group |
| A-50 | Butyl group | Cyclopentyl group |
| A-51 | Butyl group | Cyclohexyl group |
| A-52 | Butyl group | Difluoromethyl group |
| A-53 | Butyl group | Trifluoromethyl group |
| A-54 | Isobutyl group | Cyclopropyl group |
| A-55 | Isobutyl group | Cyclopentyl group |
| A-56 | Isobutyl group | Cyclohexyl group |
| A-57 | Isobutyl group | Difluoromethyl group |
| A-58 | Isobutyl group | Trifluoromethyl group |
| A-59 | sec-Isobutyl group | Cyclopropyl group |
| A-60 | sec-Isobutyl group | Cyclopentyl group |

TABLE 4

| Formula | $R^1$ | $R^2$ |
|---|---|---|
| A-61 | sec-Isobutyl group | Cyclohexyl group |
| A-62 | sec-Isobutyl group | Difluoromethyl group |
| A-63 | sec-Isobutyl group | Trifluoromethyl group |
| A-64 | tert-Isobutyl group | Cyclopropyl group |
| A-65 | tert-Isobutyl group | Cyclopentyl group |
| A-66 | tert-Isobutyl group | Cyclohexyl group |
| A-67 | tert-Isobutyl group | Difluoromethyl group |
| A-68 | tert-Isobutyl group | Trifluoromethyl group |
| A-69 | Cyclopropyl group | Cyclopentyl group |
| A-70 | Cyclopropyl group | Cyclohexyl group |
| A-71 | Cyclopropyl group | Difluoromethyl group |
| A-72 | Cyclopropyl group | Trifluoromethyl group |
| A-73 | Cyclopentyl group | Cyclohexyl group |
| A-74 | Cyclopentyl group | Difluoromethyl group |

TABLE 4-continued
| Formula | $R^1$ | $R^2$ |
|---|---|---|
| A-75 | Cyclopentyl group | Trifluoromethyl group |
| A-76 | Cyclohexyl group | Difluoromethyl group |
| A-77 | Cyclohexyl group | Trifluoromethyl group |
| A-78 | Difluoromethyl group | Trifluoromethyl group |
Next, the compounds (1) formed by the mutual bonding of $R^2$ and the ring $X^1$ are specifically illustrated below.
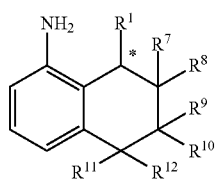
(2-1)
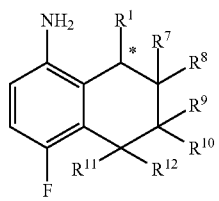
(2-2)
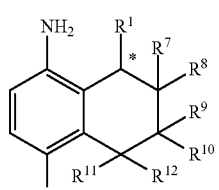
(2-3)
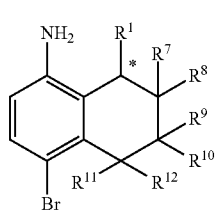
(2-4)
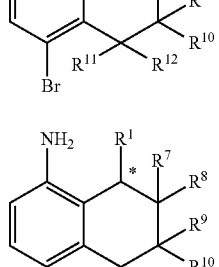
(2-5)
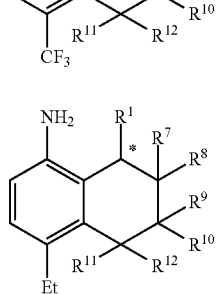
(2-6)
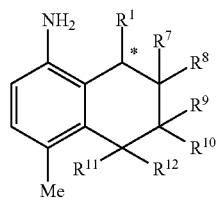
(2-7)
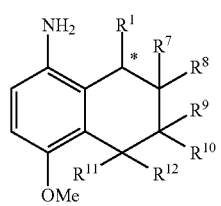
(2-8)
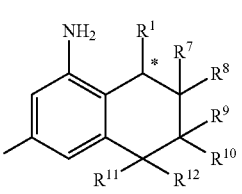
(2-9)
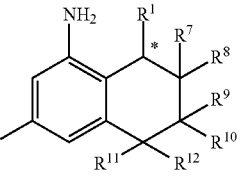
(2-10)
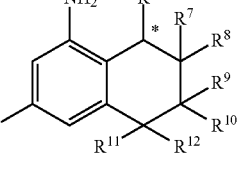
(2-11)
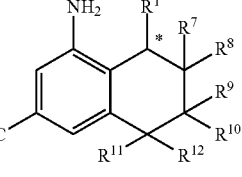
(2-12)
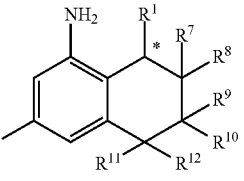
(2-13)
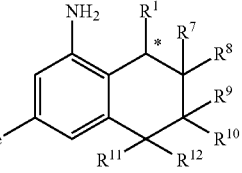
(2-14)

-continued
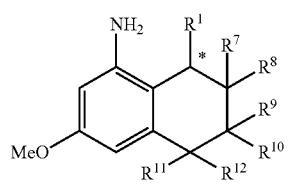 (2-15)
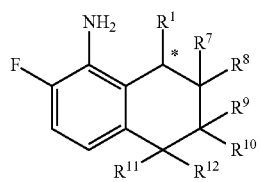 (2-16)
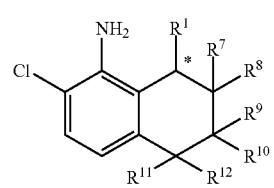 (2-17)
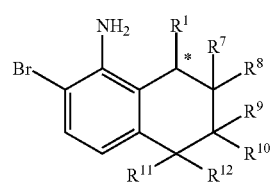 (2-18)
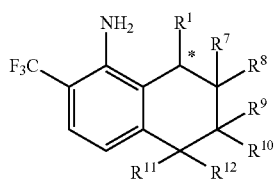 (2-19)
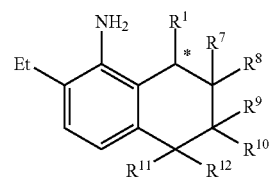 (2-20)
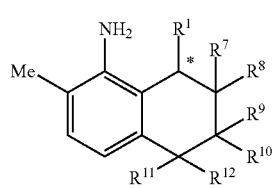 (2-21)
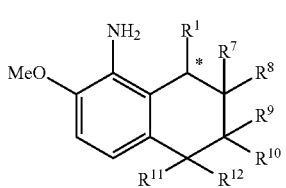 (2-22)
-continued
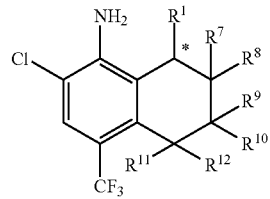 (2-23)
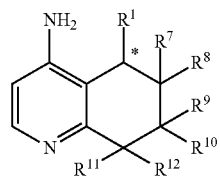 (2-24)
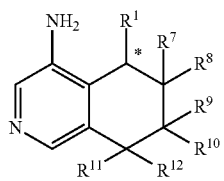 (2-25)
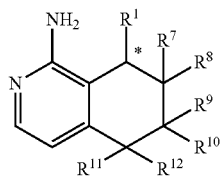 (2-26)
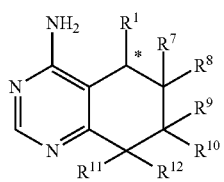 (2-27)
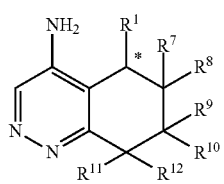 (2-28)
(2-29)
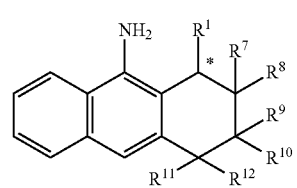 (2-30)

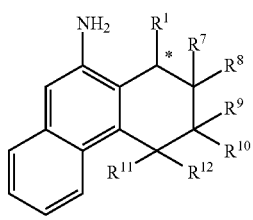
(2-31)

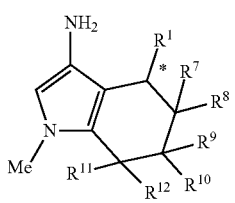
(2-32)

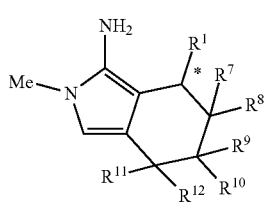
(2-33)

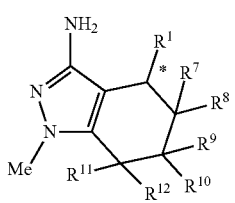
(2-34)

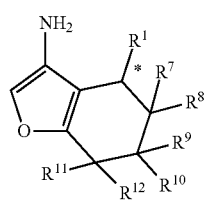
(2-35)

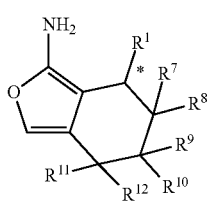
(2-36)

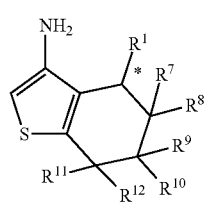
(2-37)

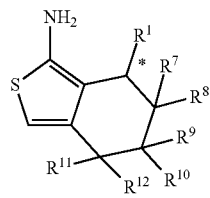
(2-38)

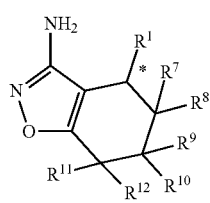
(2-39)

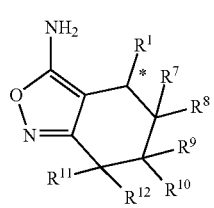
(2-40)

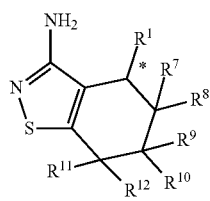
(2-41)

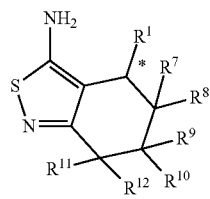
(2-42)

Examples of $R^1$, $R^2$, $R^7$, $R^8$, $R^9$, $R^{10}$, $R^{11}$, and $R^{12}$ in the compounds represented by Formulae (2-1) to (2-42) include the groups shown in Tables below. For example, the compounds represented by Formula (B-1) refer to the compounds represented by Formulae (2-1) to (2-42), in which $R^1$ is a methyl group, $R^7$ is a hydrogen atom, $R^8$ is a hydrogen atom, $R^9$ is a methyl group, $R^{10}$ is a hydrogen atom, $R^{11}$ is a hydrogen atom, and $R^{12}$ is a hydrogen atom.

TABLE 5

| Formula | R¹ | R⁷ | R⁸ | R⁹ | R¹⁰ | R¹¹ | R¹² |
|---|---|---|---|---|---|---|---|
| B-1 | Methyl group | Hydrogen | Hydrogen | Hydrogen | Hydrogen | Hydrogen | Hydrogen |
| B-2 | Methyl group | Methyl group | Methyl group | Hydrogen | Hydrogen | Hydrogen | Hydrogen |
| B-3 | Methyl group | Hydrogen | Hydrogen | Methyl group | Methyl group | Hydrogen | Hydrogen |
| B-4 | Methyl group | Hydrogen | Hydrogen | Hydrogen | Hydrogen | Methyl group | Methyl group |
| B-5 | Methyl group | Methyl group | Hydrogen | Hydrogen | Hydrogen | Hydrogen | Hydrogen |
| B-6 | Methyl group | Hydrogen | Hydrogen | Methyl group | Hydrogen | Hydrogen | Hydrogen |
| B-7 | Methyl group | Hydrogen | Hydrogen | Hydrogen | Hydrogen | Methyl group | Hydrogen |
| B-8 | Methyl group | Methyl group | Methyl group | Methyl group | Methyl group | Hydrogen | Hydrogen |
| B-9 | Methyl group | Methyl group | Methyl group | Hydrogen | Hydrogen | Methyl group | Methyl group |
| B-10 | Methyl group | Hydrogen | Hydrogen | Methyl group | Methyl group | Methyl group | Methyl group |
| B-11 | Methyl group | Methyl group | Methyl group | Methyl group | Methyl group | Methyl group | Methyl group |
| B-12 | Ethyl group | Hydrogen | Hydrogen | Hydrogen | Hydrogen | Hydrogen | Hydrogen |
| B-13 | Ethyl group | Methyl group | Methyl group | Hydrogen | Hydrogen | Hydrogen | Hydrogen |
| B-14 | Ethyl group | Hydrogen | Hydrogen | Methyl group | Methyl group | Hydrogen | Hydrogen |
| B-15 | Ethyl group | Hydrogen | Hydrogen | Hydrogen | Hydrogen | Methyl group | Methyl group |

TABLE 6

| Formula | R¹ | R⁷ | R⁸ | R⁹ | R¹⁰ | R¹¹ | R¹² |
|---|---|---|---|---|---|---|---|
| B-16 | Ethyl group | Methyl group | Hydrogen | Hydrogen | Hydrogen | Hydrogen | Hydrogen |
| B-17 | Ethyl group | Hydrogen | Hydrogen | Methyl group | Hydrogen | Hydrogen | Hydrogen |
| B-18 | Ethyl group | Hydrogen | Hydrogen | Hydrogen | Hydrogen | Methyl group | Hydrogen |
| B-19 | Ethyl group | Methyl group | Methyl group | Methyl group | Methyl group | Hydrogen | Hydrogen |
| B-20 | Ethyl group | Methyl group | Methyl group | Hydrogen | Hydrogen | Methyl group | Methyl group |
| B-21 | Ethyl group | Hydrogen | Hydrogen | Methyl group | Methyl group | Methyl group | Methyl group |
| B-22 | Ethyl group | Methyl group | Methyl group | Methyl group | Methyl group | Methyl group | Methyl group |
| B-23 | Propyl group | Hydrogen | Hydrogen | Hydrogen | Hydrogen | Hydrogen | Hydrogen |
| B-24 | Propyl group | Methyl group | Methyl group | Hydrogen | Hydrogen | Hydrogen | Hydrogen |
| B-25 | Propyl group | Hydrogen | Hydrogen | Methyl group | Methyl group | Hydrogen | Hydrogen |
| B-26 | Propyl group | Hydrogen | Hydrogen | Hydrogen | Hydrogen | Methyl group | Methyl group |
| B-27 | Propyl group | Methyl group | Hydrogen | Hydrogen | Hydrogen | Hydrogen | Hydrogen |
| B-28 | Propyl group | Hydrogen | Hydrogen | Methyl group | Hydrogen | Hydrogen | Hydrogen |
| B-29 | Propyl group | Hydrogen | Hydrogen | Hydrogen | Hydrogen | Methyl group | Hydrogen |
| B-30 | Propyl group | Methyl group | Methyl group | Methyl group | Methyl group | Hydrogen | Hydrogen |

TABLE 7

| Formula | R¹ | R⁷ | R⁸ | R⁹ | R¹⁰ | R¹¹ | R¹² |
|---|---|---|---|---|---|---|---|
| B-31 | Propyl group | Methyl group | Methyl group | Hydrogen | Hydrogen | Methyl group | Methyl group |
| B-32 | Propyl group | Hydrogen | Hydrogen | Methyl group | Methyl group | Methyl group | Methyl group |
| B-33 | Propyl group | Methyl group | Methyl group | Methyl group | Methyl group | Methyl group | Methyl group |
| B-34 | Isopropyl group | Hydrogen | Hydrogen | Hydrogen | Hydrogen | Hydrogen | Hydrogen |
| B-35 | Isopropyl group | Methyl group | Methyl group | Hydrogen | Hydrogen | Hydrogen | Hydrogen |
| B-36 | Isopropyl group | Hydrogen | Hydrogen | Methyl group | Methyl group | Hydrogen | Hydrogen |
| B-37 | Isopropyl group | Hydrogen | Hydrogen | Hydrogen | Hydrogen | Methyl group | Methyl group |
| B-38 | Isopropyl group | Methyl group | Hydrogen | Hydrogen | Hydrogen | Hydrogen | Hydrogen |
| B-39 | Isopropyl group | Hydrogen | Hydrogen | Methyl group | Hydrogen | Hydrogen | Hydrogen |
| B-40 | Isopropyl group | Hydrogen | Hydrogen | Hydrogen | Hydrogen | Methyl group | Hydrogen |
| B-41 | Isopropyl group | Methyl group | Methyl group | Methyl group | Methyl group | Hydrogen | Hydrogen |
| B-42 | Isopropyl group | Methyl group | Methyl group | Hydrogen | Hydrogen | Methyl group | Methyl group |
| B-43 | Isopropyl group | Hydrogen | Hydrogen | Methyl group | Methyl group | Methyl group | Methyl group |
| B-44 | Isopropyl group | Methyl group | Methyl group | Methyl group | Methyl group | Methyl group | Methyl group |

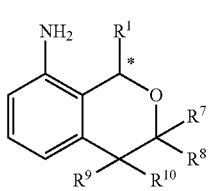

(3-1)

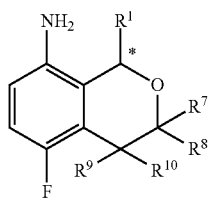

(3-2)

-continued

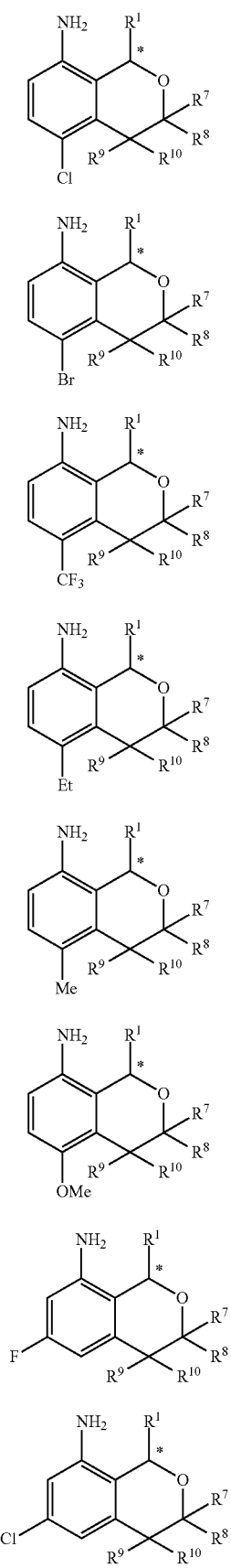
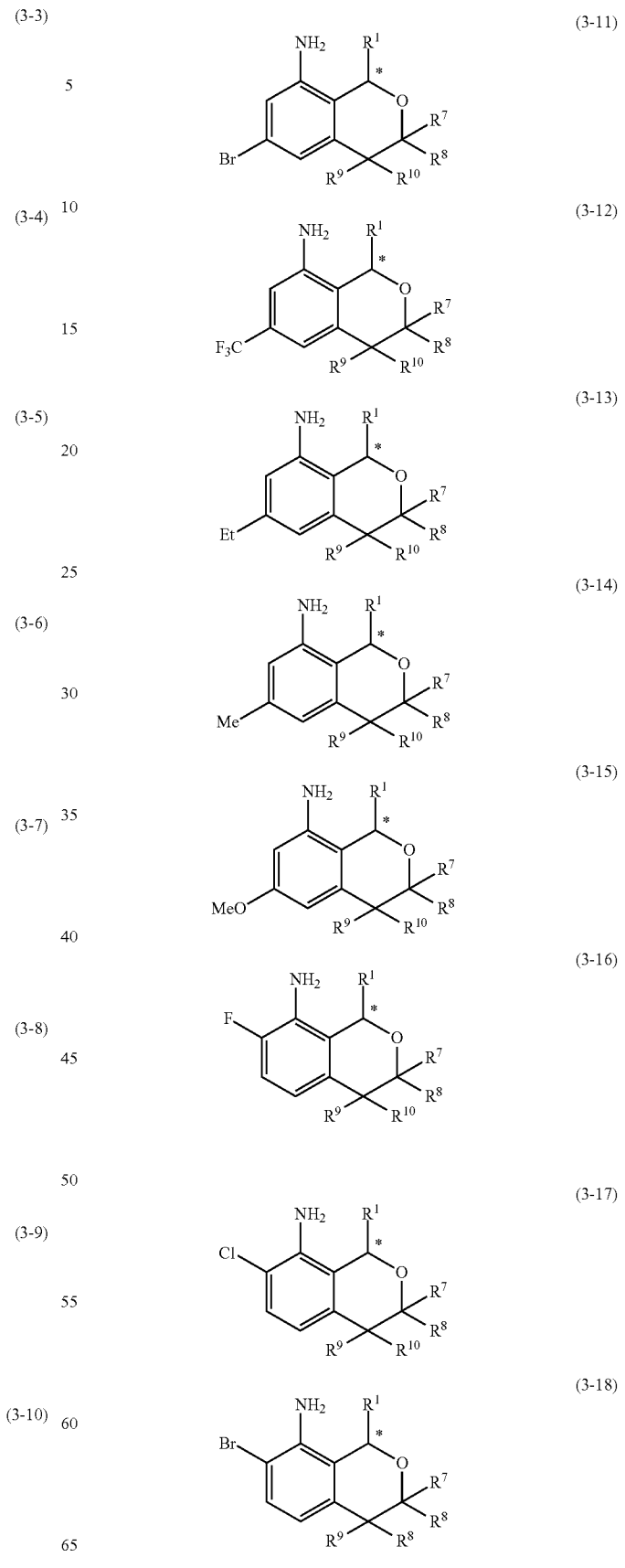

-continued (3-19) (3-20) (3-21) (3-22) (3-23) (3-24) (3-25) (3-26) (3-27) (3-28) (3-29) (3-30) (3-31) (3-32) (3-33) (3-34)

-continued

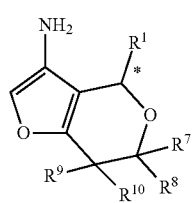
(3-35)

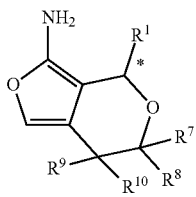
(3-36)

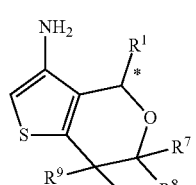
(3-37)

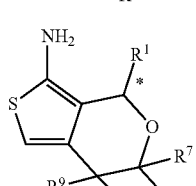
(3-38)

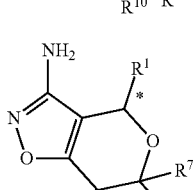
(3-39)

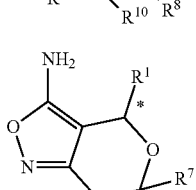
(3-40)

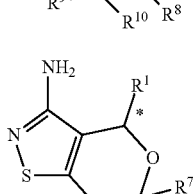
(3-41)

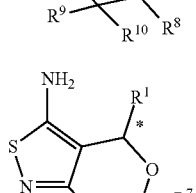
(3-42)

Examples of $R^1$, $R^7$, $R^8$, $R^9$, and $R^{10}$ in the compounds represented by Formulae (3-1) to (3-42) include the groups shown in Tables below. For example, the compounds represented by Formula (C-1) refer to the compounds represented by Formulae (3-1) to (3-42), in which $R^1$ is a methyl group, $R^7$ is a hydrogen atom, $R^8$ is a hydrogen atom, $R^9$ is a hydrogen atom, and $R^{10}$ is a hydrogen atom.

TABLE 8

| Formula | $R^1$ | $R^7$ | $R^8$ | $R^9$ | $R^{10}$ |
| --- | --- | --- | --- | --- | --- |
| C-1 | Methyl group | Hydrogen | Hydrogen | Hydrogen | Hydrogen |
| C-2 | Methyl group | Methyl group | Methyl group | Hydrogen | Hydrogen |
| C-3 | Methyl group | Hydrogen | Hydrogen | Methyl group | Methyl group |
| C-4 | Methyl group | Methyl group | Hydrogen | Hydrogen | Hydrogen |
| C-5 | Methyl group | Hydrogen | Hydrogen | Methyl group | Hydrogen |
| C-6 | Methyl group | Methyl group | Methyl group | Methyl group | Methyl group |
| C-7 | Ethyl group | Hydrogen | Hydrogen | Hydrogen | Hydrogen |
| C-8 | Ethyl group | Methyl group | Methyl group | Hydrogen | Hydrogen |
| C-9 | Ethyl group | Hydrogen | Hydrogen | Methyl group | Methyl group |
| C-10 | Ethyl group | Methyl group | Hydrogen | Hydrogen | Hydrogen |
| C-11 | Ethyl group | Hydrogen | Hydrogen | Methyl group | Hydrogen |
| C-12 | Ethyl group | Methyl group | Methyl group | Methyl group | Methyl group |
| C-13 | Propyl group | Hydrogen | Hydrogen | Hydrogen | Hydrogen |
| C-14 | Propyl group | Methyl group | Methyl group | Hydrogen | Hydrogen |
| C-15 | Propyl group | Hydrogen | Hydrogen | Methyl group | Methyl group |
| C-16 | Propyl group | Methyl group | Hydrogen | Hydrogen | Hydrogen |
| C-17 | Propyl group | Hydrogen | Hydrogen | Methyl group | Hydrogen |
| C-18 | Propyl group | Methyl group | Methyl group | Methyl group | Methyl group |
| C-19 | Isopropyl group | Hydrogen | Hydrogen | Hydrogen | Hydrogen |
| C-20 | Isopropyl group | Methyl group | Methyl group | Hydrogen | Hydrogen |
| C-21 | Isopropyl group | Hydrogen | Hydrogen | Methyl group | Methyl group |
| C-22 | Isopropyl group | Methyl group | Hydrogen | Hydrogen | Hydrogen |
| C-23 | Isopropyl group | Hydrogen | Hydrogen | Methyl group | Hydrogen |
| C-24 | Isopropyl group | Methyl group | Methyl group | Methyl group | Methyl group |

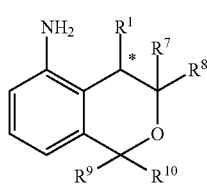
(4-1)

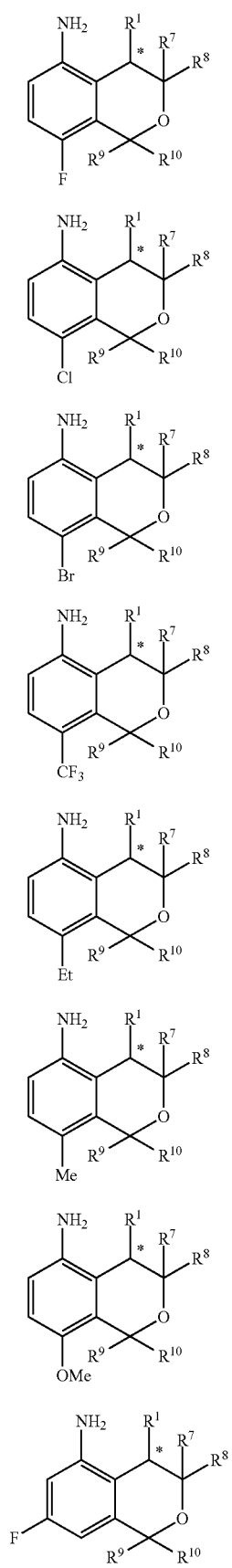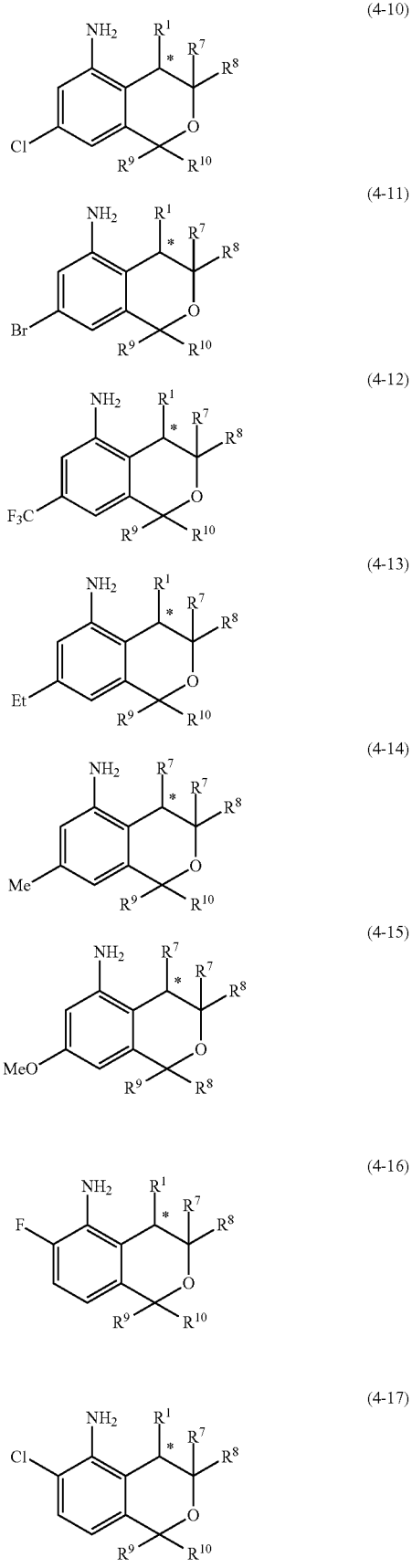

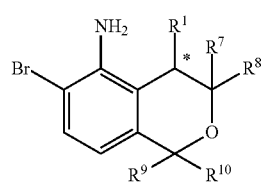
(4-18)
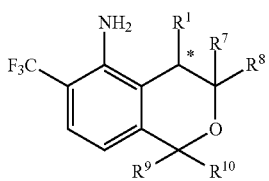
(4-19)
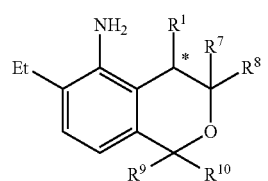
(4-20)
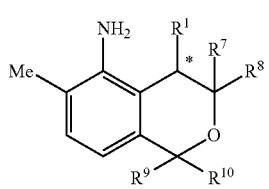
(4-21)
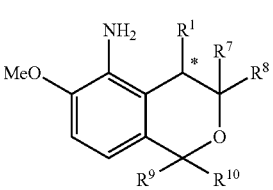
(4-22)
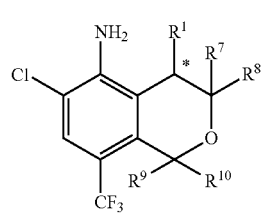
(4-23)
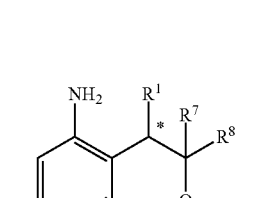
(4-24)
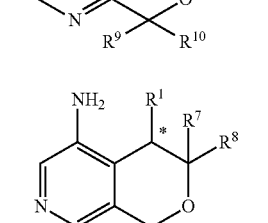
(4-25)
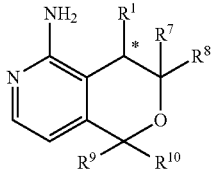
(4-26)
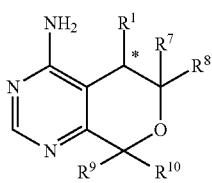
(4-27)
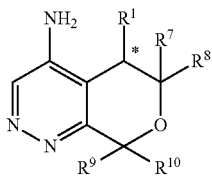
(4-28)
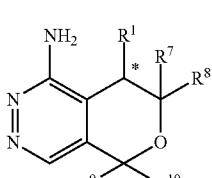
(4-29)
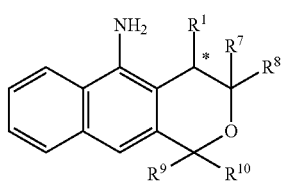
(4-30)
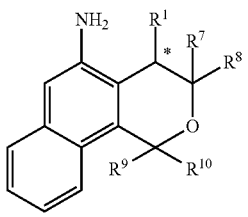
(4-31)
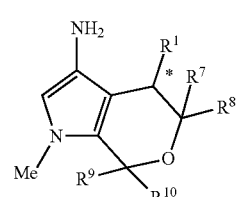
(4-32)
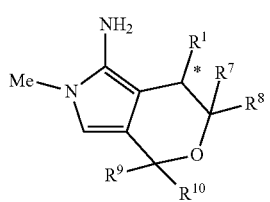
(4-33)

-continued (4-34) 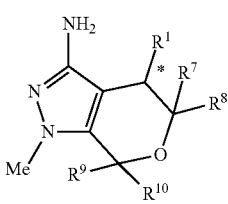

(4-35) 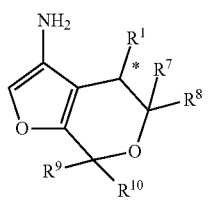

(4-36) 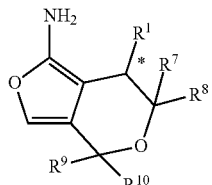

(4-37) 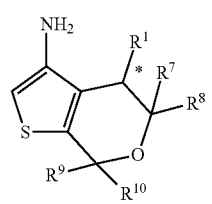

(4-38) 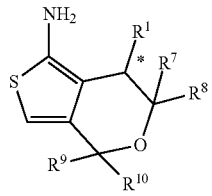

(4-39) 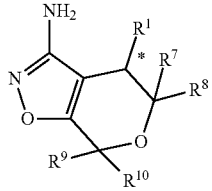

(4-40) 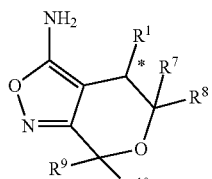

(4-41) 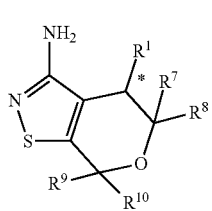

-continued (4-42) 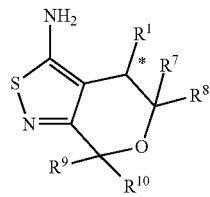

Examples of $R^1$, $R^7$, $R^8$, $R^9$, and $R^{10}$ in the compounds represented by Formulae (4-1) to (4-42) include the groups shown in Tables below. For example, the compounds represented by Formula (D-1) refer to the compounds represented by Formulae (4-1) to (4-42), in which $R^1$ is a methyl group, $R^7$ is a hydrogen atom, $R^8$ is a hydrogen atom, $R^9$ is a hydrogen atom, and $R^{10}$ is a hydrogen atom.

TABLE 9

| Formula | $R^1$ | $R^7$ | $R^8$ | $R^9$ | $R^{10}$ |
| --- | --- | --- | --- | --- | --- |
| D-1 | Methyl group | Hydrogen | Hydrogen | Hydrogen | Hydrogen |
| D-2 | Methyl group | Methyl group | Methyl group | Hydrogen | Hydrogen |
| D-3 | Methyl group | Hydrogen | Hydrogen | Methyl group | Methyl group |
| D-4 | Methyl group | Methyl group | Hydrogen | Hydrogen | Hydrogen |
| D-5 | Methyl group | Hydrogen | Hydrogen | Methyl group | Hydrogen |
| D-6 | Methyl group | Methyl group | Methyl group | Methyl group | Methyl group |
| D-7 | Ethyl group | Hydrogen | Hydrogen | Hydrogen | Hydrogen |
| D-8 | Ethyl group | Methyl group | Methyl group | Hydrogen | Hydrogen |
| D-9 | Ethyl group | Hydrogen | Hydrogen | Methyl group | Methyl group |
| D-10 | Ethyl group | Methyl group | Hydrogen | Hydrogen | Hydrogen |
| D-11 | Ethyl group | Hydrogen | Hydrogen | Methyl group | Hydrogen |
| D-12 | Ethyl group | Methyl group | Methyl group | Methyl group | Methyl group |
| D-13 | Propyl group | Hydrogen | Hydrogen | Hydrogen | Hydrogen |
| D-14 | Propyl group | Methyl group | Methyl group | Hydrogen | Hydrogen |
| D-15 | Propyl group | Hydrogen | Hydrogen | Methyl group | Methyl group |
| D-16 | Propyl group | Methyl group | Hydrogen | Hydrogen | Hydrogen |
| D-17 | Propyl group | Hydrogen | Hydrogen | Methyl group | Hydrogen |
| D-18 | Propyl group | Methyl group | Methyl group | Methyl group | Methyl group |
| D-19 | Isopropyl group | Hydrogen | Hydrogen | Hydrogen | Hydrogen |
| D-20 | Isopropyl group | Methyl group | Methyl group | Hydrogen | Hydrogen |
| D-21 | Isopropyl group | Hydrogen | Hydrogen | Methyl group | Methyl group |
| D-22 | Isopropyl group | Methyl group | Hydrogen | Hydrogen | Hydrogen |
| D-23 | Isopropyl group | Hydrogen | Hydrogen | Methyl group | Hydrogen |
| D-24 | Isopropyl group | Methyl group | Methyl group | Methyl group | Methyl group |

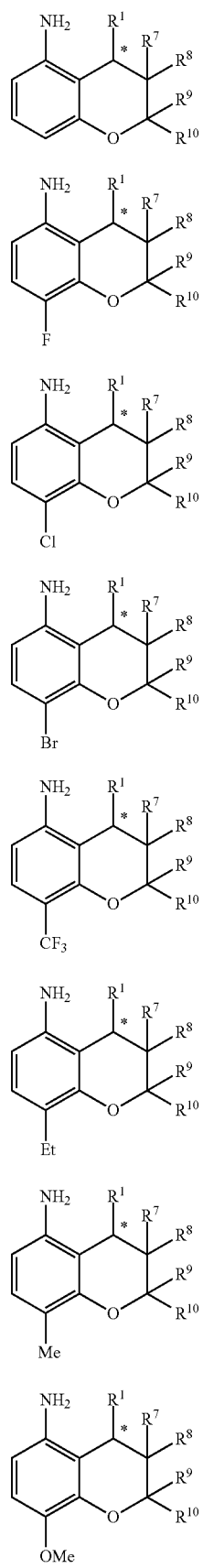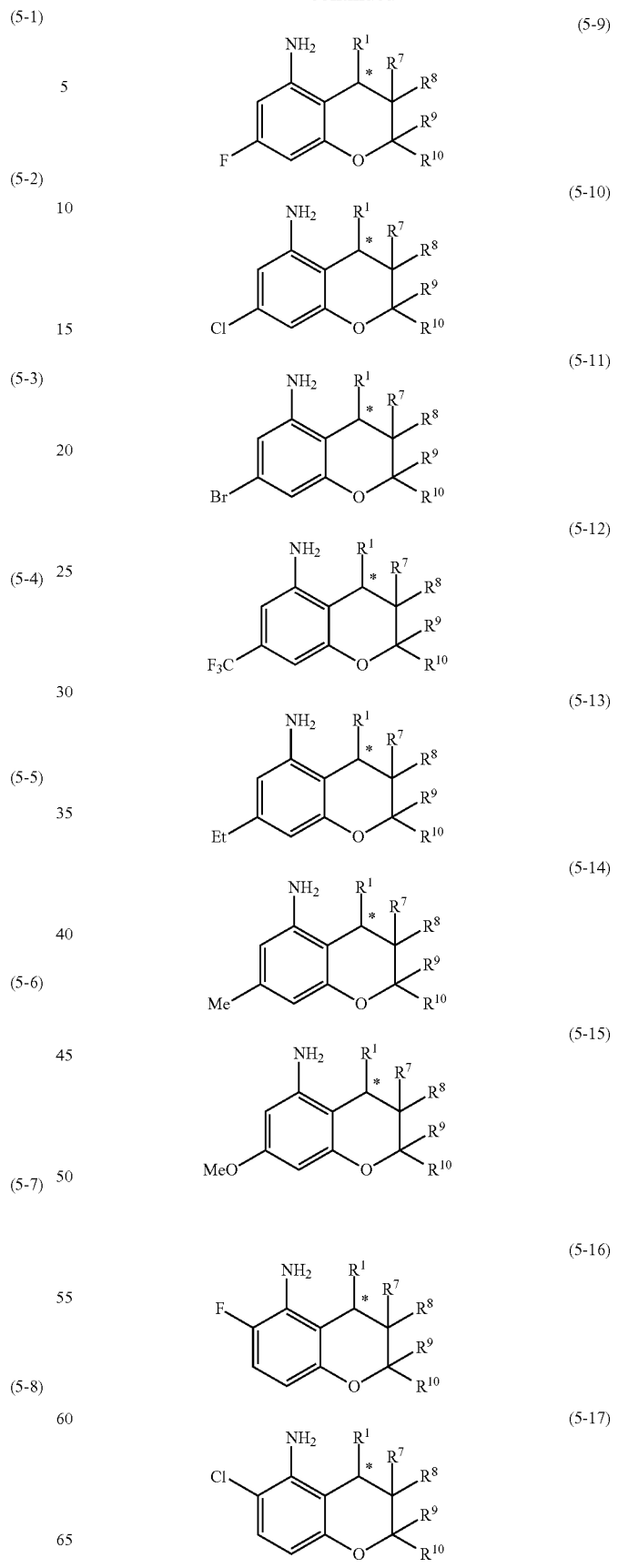

-continued
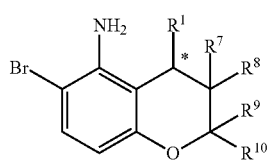 (5-18)
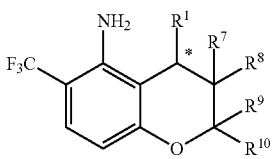 (5-19)
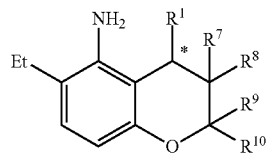 (5-20)
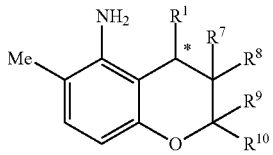 (5-21)
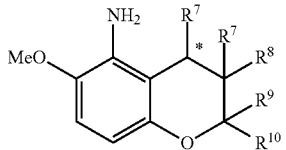 (5-22)
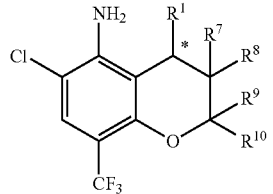 (5-23)
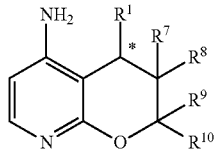 (5-24)
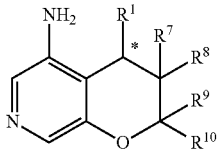 (5-25)
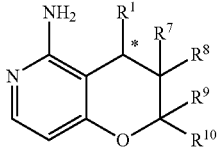 (5-26)
-continued
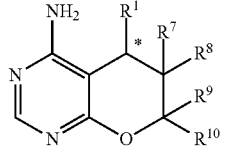 (5-27)
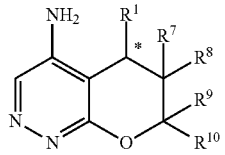 (5-28)
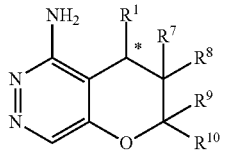 (5-29)
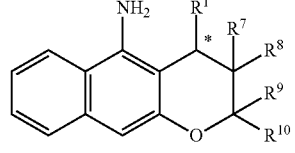 (5-30)
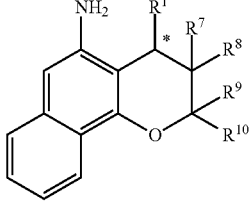 (5-31)
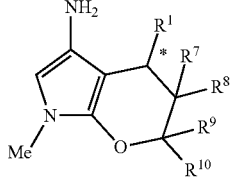 (5-32)
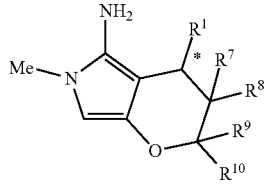 (5-33)
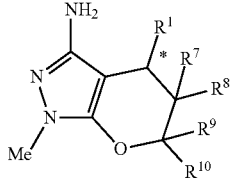 (5-34)

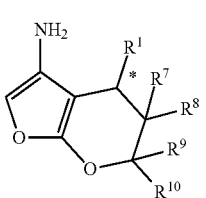

(5-35)

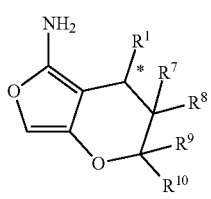

(5-36)

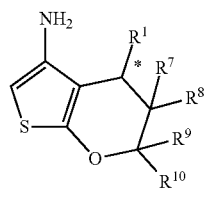

(5-37)

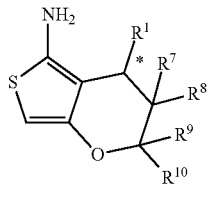

(5-38)

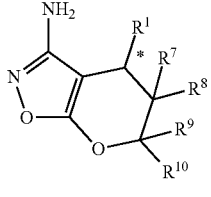

(5-39)

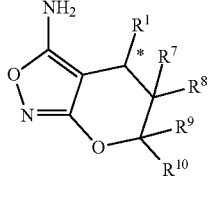

(5-40)

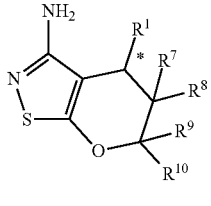

(5-41)

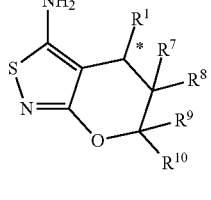

(5-42)

Examples of $R^1$, $R^7$, $R^8$, $R^9$, and $R^{10}$ in the compounds represented by Formulae (5-1) to (5-42) include the groups shown in Tables below. For example, the compounds represented by Formula (E-1) refer to the compounds represented by Formulae (5-1) to (5-42), in which $R^1$ is a methyl group, $R^7$ is a hydrogen atom, $R^8$ is a hydrogen atom, $R^9$ is a hydrogen atom, and $R^{10}$ is a hydrogen atom.

TABLE 10

| Formula | $R^1$ | $R^7$ | $R^8$ | $R^9$ | $R^{10}$ |
|---|---|---|---|---|---|
| E-1 | Methyl group | Hydrogen | Hydrogen | Hydrogen | Hydrogen |
| E-2 | Methyl group | Methyl group | Methyl group | Hydrogen | Hydrogen |
| E-3 | Methyl group | Hydrogen | Hydrogen | Methyl group | Methyl group |
| E-4 | Methyl group | Methyl group | Hydrogen | Hydrogen | Hydrogen |
| E-5 | Methyl group | Hydrogen | Hydrogen | Methyl group | Hydrogen |
| E-6 | Methyl group | Methyl group | Methyl group | Methyl group | Methyl group |
| E-7 | Ethyl group | Hydrogen | Hydrogen | Hydrogen | Hydrogen |
| E-8 | Ethyl group | Methyl group | Methyl group | Hydrogen | Hydrogen |
| E-9 | Ethyl group | Hydrogen | Hydrogen | Methyl group | Methyl group |
| E-10 | Ethyl group | Methyl group | Hydrogen | Hydrogen | Hydrogen |
| E-11 | Ethyl group | Hydrogen | Hydrogen | Methyl group | Hydrogen |
| E-12 | Ethyl group | Methyl group | Methyl group | Methyl group | Methyl group |
| E-13 | Propyl group | Hydrogen | Hydrogen | Hydrogen | Hydrogen |
| E-14 | Propyl group | Methyl group | Methyl group | Hydrogen | Hydrogen |
| E-15 | Propyl group | Hydrogen | Hydrogen | Methyl group | Methyl group |
| E-16 | Propyl group | Methyl group | Hydrogen | Hydrogen | Hydrogen |
| E-17 | Propyl group | Hydrogen | Hydrogen | Methyl group | Hydrogen |
| E-18 | Propyl group | Methyl group | Methyl group | Methyl group | Methyl group |
| E-19 | Isopropyl group | Hydrogen | Hydrogen | Hydrogen | Hydrogen |
| E-20 | Isopropyl group | Methyl group | Methyl group | Hydrogen | Hydrogen |
| E-21 | Isopropyl group | Hydrogen | Hydrogen | Methyl group | Methyl group |
| E-22 | Isopropyl group | Methyl group | Hydrogen | Hydrogen | Hydrogen |
| E-23 | Isopropyl group | Hydrogen | Hydrogen | Methyl group | Hydrogen |
| E-24 | Isopropyl group | Methyl group | Methyl group | Methyl group | Methyl group |

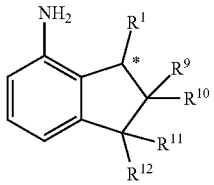

(6-1)

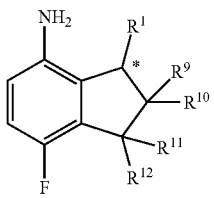

(6-2)

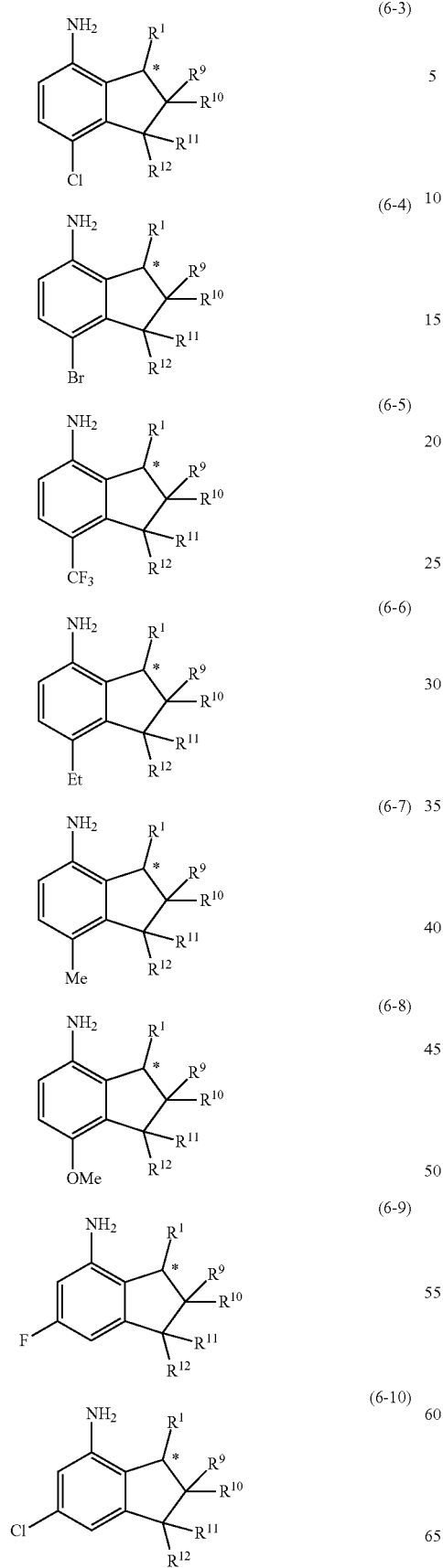
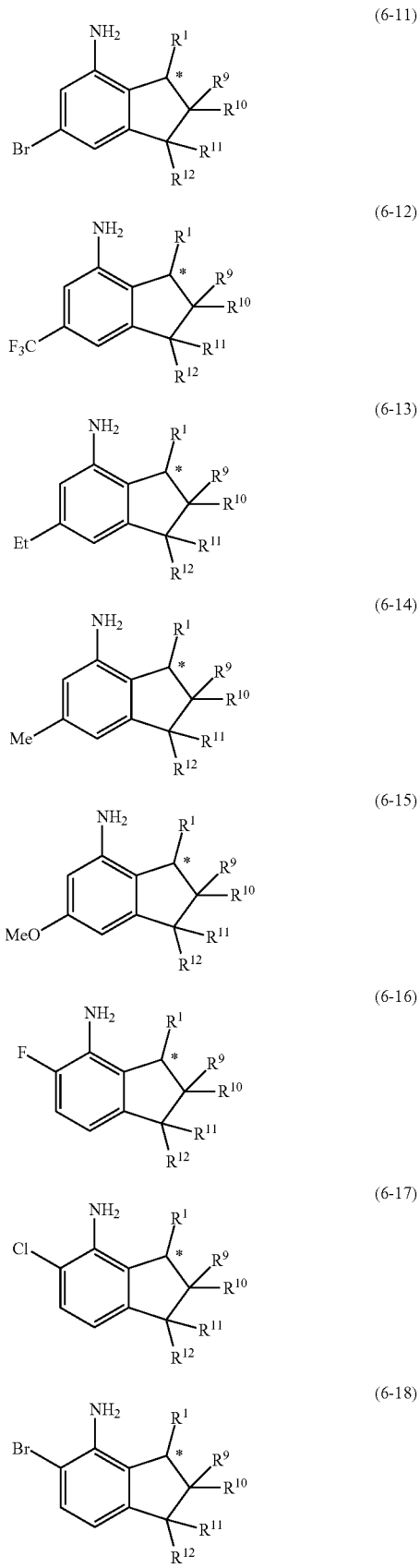

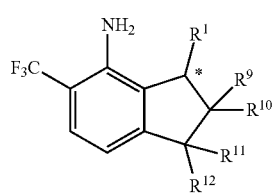
(6-19)
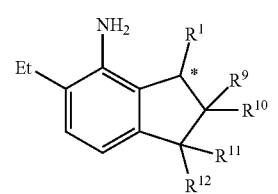
(6-20)
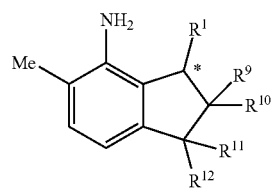
(6-21)
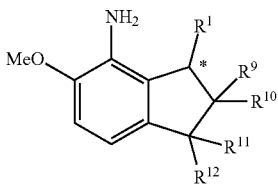
(6-22)
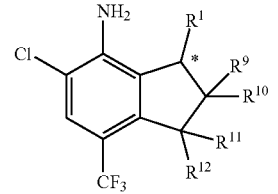
(6-23)
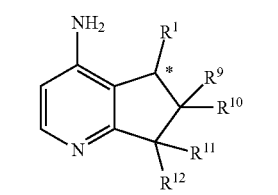
(6-24)
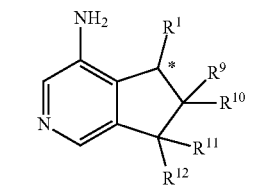
(6-25)
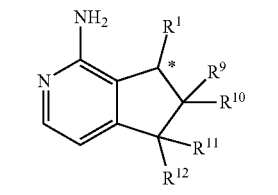
(6-26)
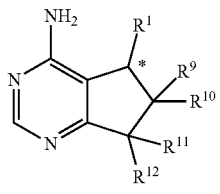
(6-27)
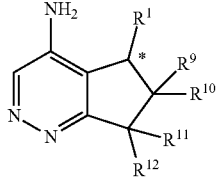
(6-28)
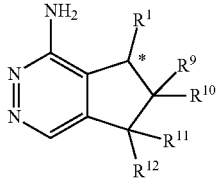
(6-29)
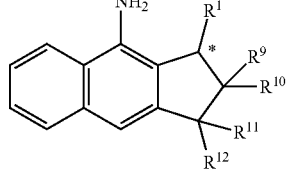
(6-30)
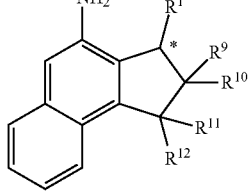
(6-31)
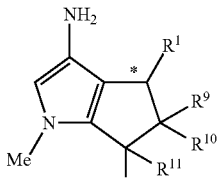
(6-32)
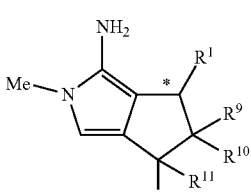
(6-33)
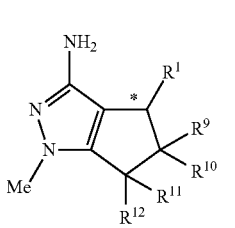
(6-34)

-continued (6-35) 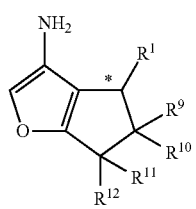

(6-36) 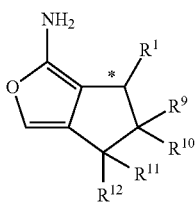

(6-37) 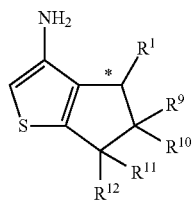

(6-38) 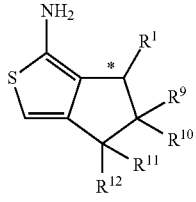

(6-39) 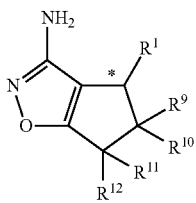

(6-40) 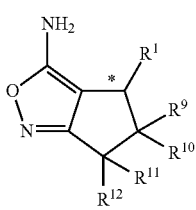

(6-41) 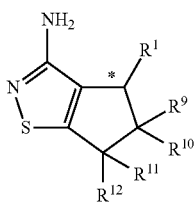

(6-42) 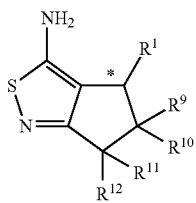

Examples of $R^1$, $R^9$, $R^{10}$, $R^{11}$, and $R^{12}$ in the compounds represented by Formulae (6-1) to (6-42) include the groups shown in Tables below. For example, the compounds represented by Formula (F-1) refer to the compounds represented by Formulae (6-1) to (6-42), in which $R^1$ is a methyl group, $R^9$ is a hydrogen atom, $R^{10}$ is a hydrogen atom, $R^{11}$ is a hydrogen atom, and $R^{12}$ is a hydrogen atom.

TABLE 11

| Formula | $R^1$ | $R^9$ | $R^{10}$ | $R^{11}$ | $R^{12}$ |
|---|---|---|---|---|---|
| F-1 | Methyl group | Hydrogen | Hydrogen | Hydrogen | Hydrogen |
| F-2 | Methyl group | Methyl group | Methyl group | Hydrogen | Hydrogen |
| F-3 | Methyl group | Hydrogen | Hydrogen | Methyl group | Methyl group |
| F-4 | Methyl group | Methyl group | Hydrogen | Hydrogen | Hydrogen |
| F-5 | Methyl group | Hydrogen | Hydrogen | Methyl group | Hydrogen |
| F-6 | Methyl group | Methyl group | Methyl group | Methyl group | Methyl group |
| F-7 | Ethyl group | Hydrogen | Hydrogen | Hydrogen | Hydrogen |
| F-8 | Ethyl group | Methyl group | Methyl group | Hydrogen | Hydrogen |
| F-9 | Ethyl group | Hydrogen | Hydrogen | Methyl group | Methyl group |
| F-10 | Ethyl group | Methyl group | Hydrogen | Hydrogen | Hydrogen |
| F-11 | Ethyl group | Hydrogen | Hydrogen | Methyl group | Hydrogen |
| F-12 | Ethyl group | Methyl group | Methyl group | Methyl group | Methyl group |
| F-13 | Propyl group | Hydrogen | Hydrogen | Hydrogen | Hydrogen |
| F-14 | Propyl group | Methyl group | Methyl group | Hydrogen | Hydrogen |
| F-15 | Propyl group | Hydrogen | Hydrogen | Methyl group | Methyl group |
| F-16 | Propyl group | Methyl group | Hydrogen | Hydrogen | Hydrogen |
| F-17 | Propyl group | Hydrogen | Hydrogen | Methyl group | Hydrogen |
| F-18 | Propyl group | Methyl group | Methyl group | Methyl group | Methyl group |
| F-19 | Isopropyl group | Hydrogen | Hydrogen | Hydrogen | Hydrogen |
| F-20 | Isopropyl group | Methyl group | Methyl group | Hydrogen | Hydrogen |
| F-21 | Isopropyl group | Hydrogen | Hydrogen | Methyl group | Methyl group |
| F-22 | Isopropyl group | Methyl group | Methyl group | Hydrogen | Hydrogen |
| F-23 | Isopropyl group | Hydrogen | Hydrogen | Methyl group | Hydrogen |
| F-24 | Isopropyl group | Methyl group | Methyl group | Methyl group | Methyl group |

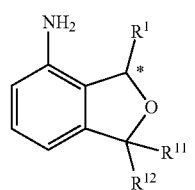 (7-1)
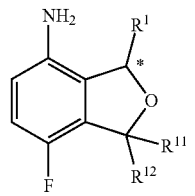 (7-2)
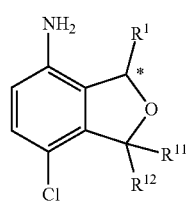 (7-3)
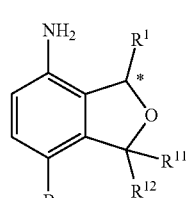 (7-4)
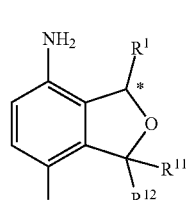 (7-5)
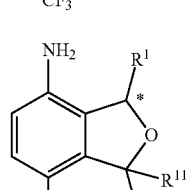 (7-6)
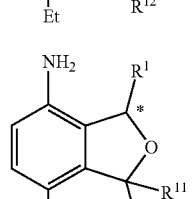 (7-7)
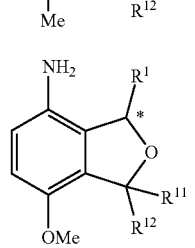 (7-8)
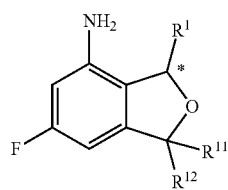 (7-9)
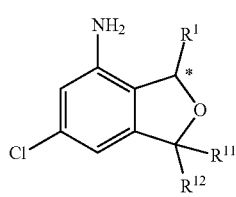 (7-10)
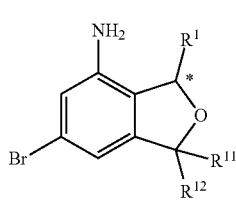 (7-11)
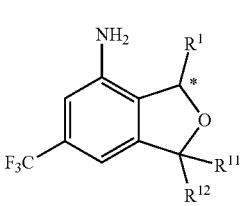 (7-12)
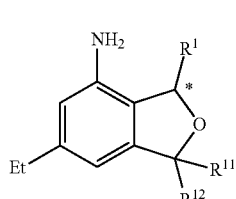 (7-13)
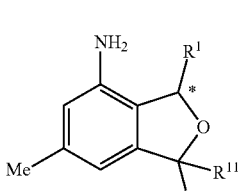 (7-14)
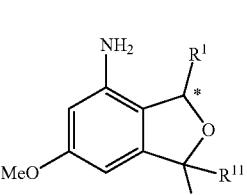 (7-15)
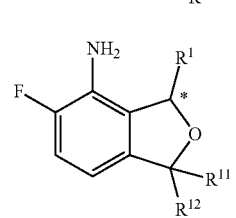 (7-16)

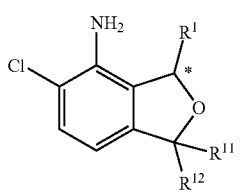 (7-17)
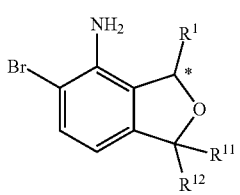 (7-18)
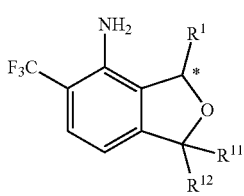 (7-19)
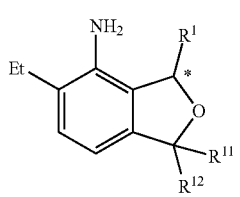 (7-20)
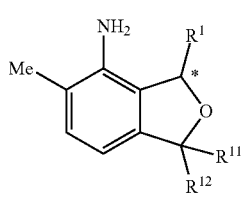 (7-21)
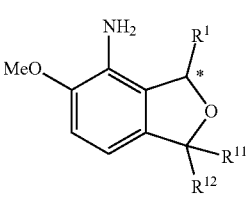 (7-22)
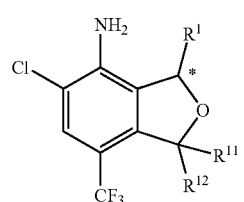 (7-23)
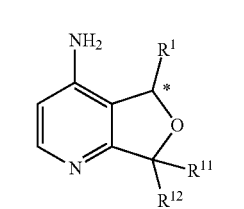 (7-24)
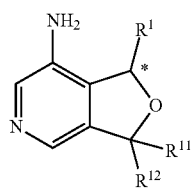 (7-25)
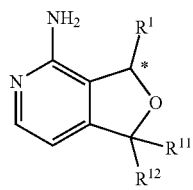 (7-26)
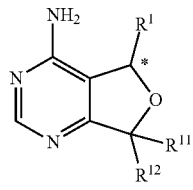 (7-27)
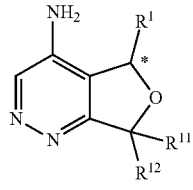 (7-28)
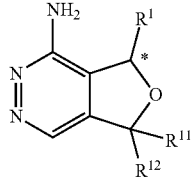 (7-29)
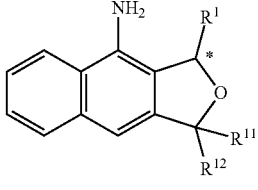 (7-30)
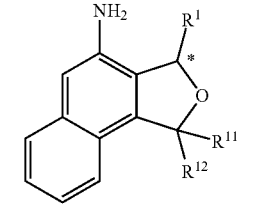 (7-31)
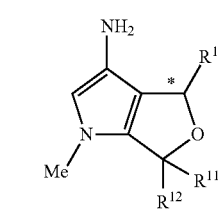 (7-32)

(7-33) 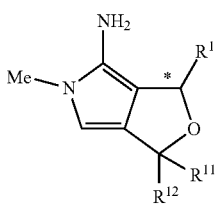

(7-34) 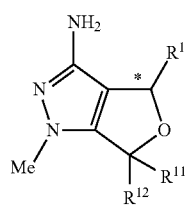

(7-35) 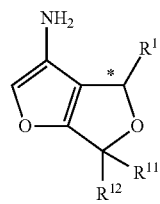

(7-36) 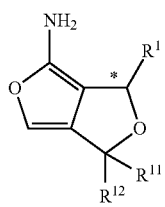

(7-37) 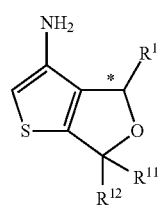

(7-38) 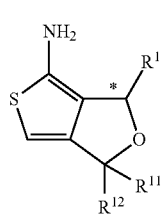

(7-39) 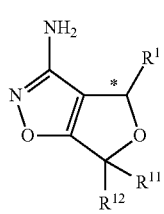

(7-40) 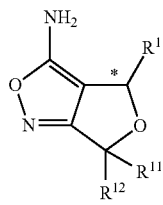

(7-41) 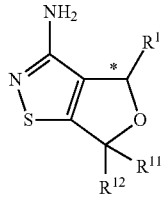

(7-42) 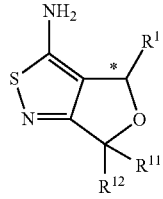

Examples of $R^1$, $R^{11}$, and $R^{12}$ in the compounds represented by Formulae (7-1) to (7-42) include the groups shown in Tables below. For example, the compounds represented by Formula (G-1) refer to the compounds represented by Formulae (7-1) to (7-42), in which $R^1$ is a methyl group, $R^{11}$ is a hydrogen atom, and $R^{12}$ is a hydrogen atom.

TABLE 12

| Formula | $R^1$ | $R^{11}$ | $R^{12}$ |
|---|---|---|---|
| G-1 | Methyl group | Hydrogen | Hydrogen |
| G-2 | Methyl group | Methyl group | Hydrogen |
| G-3 | Methyl group | Methyl group | Methyl group |
| G-4 | Ethyl group | Hydrogen | Hydrogen |
| G-5 | Ethyl group | Hydrogen | Hydrogen |
| G-6 | Ethyl group | Methyl group | Methyl group |
| G-7 | Propyl group | Hydrogen | Hydrogen |
| G-8 | Propyl group | Hydrogen | Hydrogen |
| G-9 | Propyl group | Methyl group | Methyl group |
| G-10 | Isopropyl group | Hydrogen | Hydrogen |
| G-11 | Isopropyl group | Hydrogen | Hydrogen |
| G-12 | Isopropyl group | Methyl group | Methyl group |

(8-1) 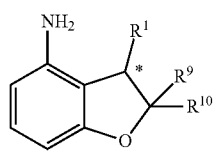

(8-2) 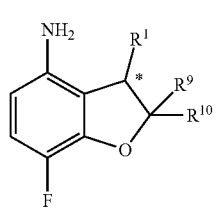

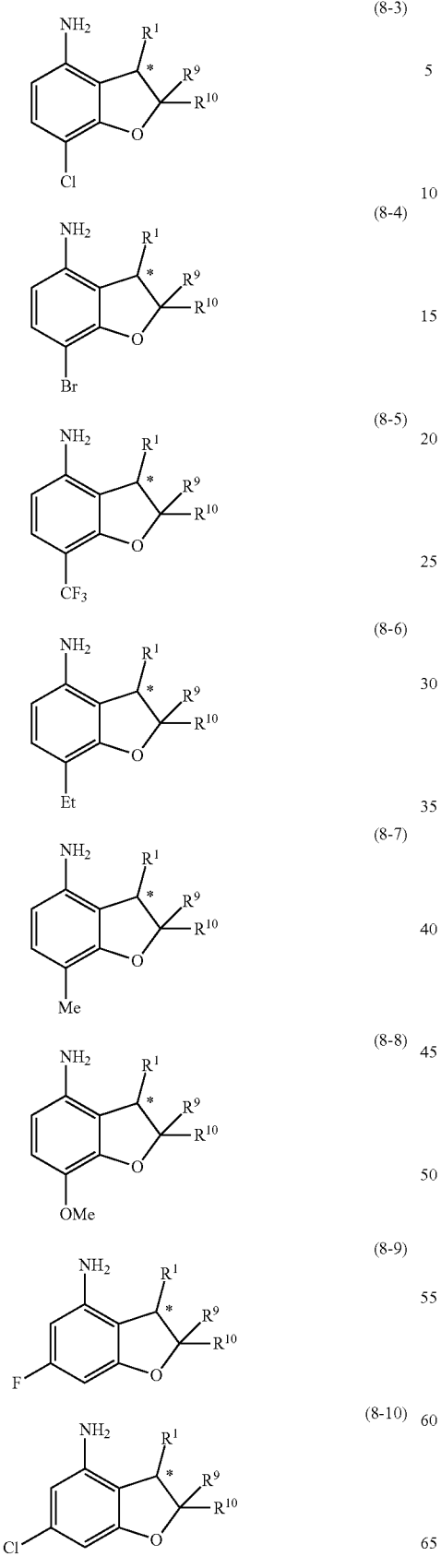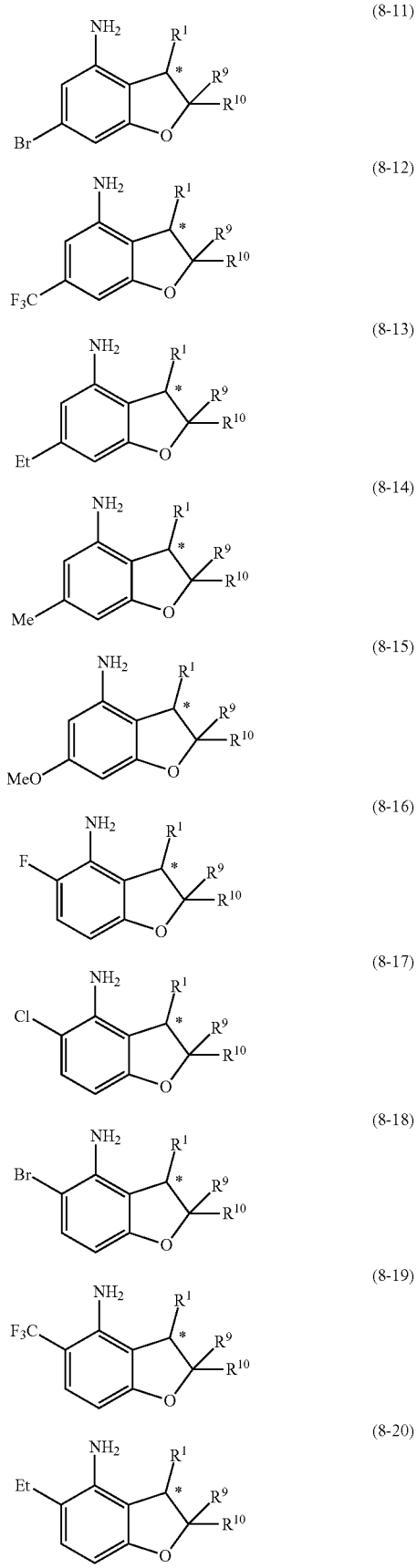

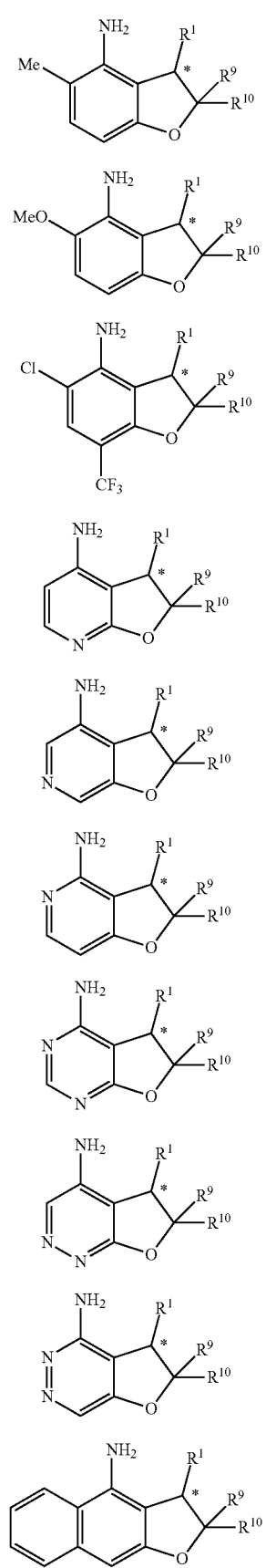
(8-21)
(8-22)
(8-23)
(8-24)
(8-25)
(8-26)
(8-27)
(8-28)
(8-29)
(8-30)
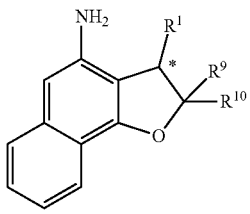
(8-31)
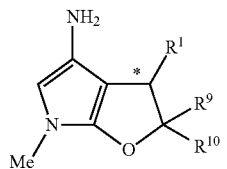
(8-32)
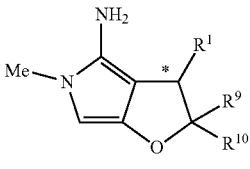
(8-33)
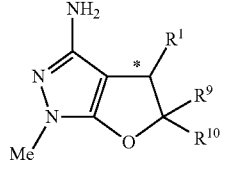
(8-34)
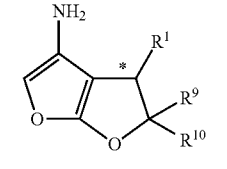
(8-35)
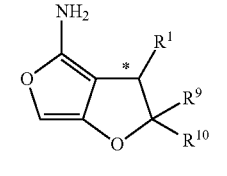
(8-36)
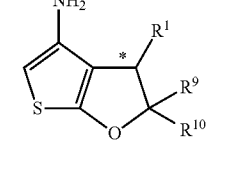
(8-37)
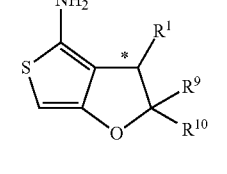
(8-38)
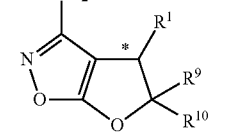
(8-39)

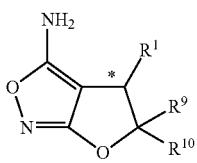

(8-40)

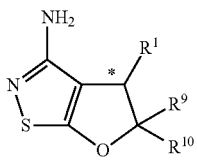

(8-41)

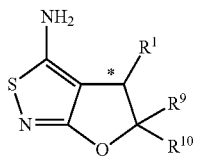

(8-42)

Examples of $R^1$, $R^9$, $R^{10}$, $R^{11}$, and $R^{12}$ in the compounds represented by Formulae (8-1) to (8-42) include the groups shown in Tables below. For example, the compounds represented by Formula (H-1) refer to the compounds represented by Formulae (8-1) to (8-42), in which $R^1$ is a methyl group, $R^9$ is a hydrogen atom, and $R^{10}$ is a hydrogen atom.

TABLE 13

| Formula | $R^1$ | $R^9$ | $R^{10}$ |
| --- | --- | --- | --- |
| H-1 | Methyl group | Hydrogen | Hydrogen |
| H-2 | Methyl group | Methyl group | Hydrogen |
| H-3 | Methyl group | Methyl group | Methyl group |
| H-4 | Ethyl group | Hydrogen | Hydrogen |
| H-5 | Ethyl group | Hydrogen | Hydrogen |
| H-6 | Ethyl group | Methyl group | Methyl group |
| H-7 | Propyl group | Hydrogen | Hydrogen |
| H-8 | Propyl group | Hydrogen | Hydrogen |
| H-9 | Propyl group | Methyl group | Methyl group |
| H-10 | Isopropyl group | Hydrogen | Hydrogen |
| H-11 | Isopropyl group | Hydrogen | Hydrogen |
| H-12 | Isopropyl group | Methyl group | Methyl group |

Among the compounds represented by Formulae (1-1) to (1~199), preferred are the compounds represented by Formulae (A-1) to (A-28).

Among the compounds represented by Formulae (2-1) to (2~23), preferred are the compounds represented by Formulae (B-1) to (B-44).

Among the compounds represented by Formulae (6-1) to (6~23), preferred are the compounds represented by Formulae (F-1) to (F-24).

Among the compounds represented by Formulae (6-1) to (6~23), more preferred are the compounds represented by Formulae (F-3), (F-9), (F-15), and (F-21).

Among the compounds represented by Formula (1), the compound represented by Formula (3) is particularly preferred.

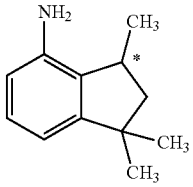

(3)

An optically active form of the compound represented by Formula (1) can be produced according to a known synthesis method or is commercially available. The optical purity of the optically active form is usually from 20% ee to 100% ee, and preferably from 20% ee to 99% ee.

The racemate of the compound represented by Formula (1) produced by bringing a transition metal catalyst into contact with an, optically active form of the compound represented by Formula (1) has an optical purity of 0% ee to 5% ee.

Examples of the transition metal catalyst include platinum catalysts such as platinum black, colloidal platinum, platinum oxide, and platinum-barium sulfate; nickel catalysts such as reduced nickel, Urushibara nickel, nickel formate, Raney nickel, and nickel-diatomaceous earth; palladium catalysts such as palladium-carbon, palladium-calcium carbonate, palladium-alumina, and palladium-platinum-carbon; cobalt catalysts such as Raney cobalt; iron catalysts such as Raney iron; and copper catalysts such as copper chromite, and two or more kinds of the transition metal catalysts may be used together. Preferred transition metal catalyst is a palladium catalyst, and more preferred are palladium-carbon, palladium-alumina, or palladium-platinum-carbon.

The transition metal catalyst may be supported on a carrier. Examples of the carrier include activated carbon, silica, zeolite, and Celite (registered trademark).

The transition metal catalyst may be used after hydrogen is absorbed in the transition metal catalyst in the coexistence of the transition metal catalyst and hydrogen, and the hydrogen absorbing transition metal catalyst is preferred.

The amount of the transition metal catalyst to be used is usually from 0.001 part by weight to 1 part by weight, and preferably from 0.005 part by weight to 0.5 part by weight, per part by weight of the optically active form of the compound represented by Formula (1).

The contact between the transition metal catalyst and the optically active form of the compound represented by Formula (1) may be carried out in the presence of a solvent or in the absence of a solvent.

Examples of the solvent include aromatic solvents such as benzene, chlorobenzene, toluene, xylene, and pyridine; halogenated hydrocarbon solvents such as chloroform and dichloromethane; ester solvents such as ethyl acetate; ketone solvent such as acetone, methyl ethyl ketone, and methyl isobutyl ketone; ether solvents such as 1,2-dimethoxy ethane, diethylene glycol dimethyl ether, polyethylene glycol, tetrahydrofuran, and dioxane; nitrile solvents such as acetonitrile and propionitrile; sulfoxide solvents such as dimethyl sulfoxide; amide solvents such as dimethylacetamide and N-methyl pyrrolidone; alcohol solvents such as methanol, ethanol, and 2-propanol; aqueous solvents such as water, an aqueous sodium hydroxide solution, and aqueous ammonia; and a mixture of solvents. Preferred solvent is the alcohol solvent, and more preferred is 2-propanol.

The amount of the solvent to be used is usually 100 parts by weight or less, and preferably 5 parts by weight or less, per part by weight of the optically active form of the compound represented by Formula (1).

The contact between the transition metal catalyst and the optically active form of the compound represented by Formula (1) may be carried out in the presence of an additive which will become a hydrogen source.

Examples of the additive include formic acid; formates such as ammonium formate and sodium formate; cyclohexene; cyclohexene compounds such as 3-methyl-1-cyclohexene and 4-methyl-1-cyclohexene; 1,3-cyclohexadiene; 1,4-cyclohexadiene; octalin such as 1,2,3,4,4aα,5,8,8αβ-octahydronaphthalene, 1,2,3,4,5,6,7,8-octahydronaphthalene, 1-methyl-octalin, and trans-2-methyloctalin; tetralin; 1,6-dimethyl tetralin; 6-methyl tetralin; limonene; pinene; 3-carene; phellandrene; terpinolene; 1-p-menthene; cadalene; pulegone; selinene; alcohol compounds such as methanol, ethanol, 2-propanol, and cyclohexanol; or a mixture thereof, and preferred are cyclohexene compounds, and more preferred is cyclohexene.

The amount of the additive to be used is usually from 10 parts by weight or less, preferably 5 parts by weight or less, and more preferably 2 parts by weight or less, per part by weight of the optically active form of the compound represented by Formula (1).

A compound serving as an additive which will become a hydrogen source as well as a solvent may be used. As the compound serving as an additive which will become a hydrogen source as well as a solvent additive which will become a hydrogen source, an alcohol compound is preferred, and 2-propanol is more preferred.

The production method of the present invention is carried out by bringing a transition metal catalyst into contact with an optically active form of the compound represented by Formula (1), and it is preferable that the transition metal catalyst and the optically active form of the compound represented by Formula (1) are mixed in the presence of hydrogen, and the obtained mixture is heated.

The contact between the transition metal catalyst and the optically active form of the compound represented by Formula (1) may be carried out in a sealed container such as an autoclave or in an open container such as a flask. The contact between the transition metal catalyst and the optically active form of the compound represented by Formula (1) may be carried out in air or in a nitrogen or hydrogen atmosphere, and preferably in a nitrogen or hydrogen atmosphere.

The temperature for the contact between the transition metal catalyst and the optically active form of the compound represented by Formula (1) is usually 20° C. or higher, preferably 80° C. or higher, and more preferably 100° C. or higher. Further, the contact temperature is usually 250° C. or lower, preferably 200° C. or lower, more preferably 190° C. or lower, and particularly preferably 170° C. or lower.

The contact between the transition metal catalyst and the optically active form of the compound represented by Formula (1) is preferably carried out by mixing them at 50° C. to 80° C., heating the mixture to 100° C. to 200° C., and preferably 150° C. to 200° C. in a hydrogen atmosphere, and more preferably carried out by mixing them at 50° C. to 80° C. in a hydrogen atmosphere, replacing hydrogen with nitrogen, and then heating the mixture to 100° C. to 200° C., and preferably 150° C. to 200° C.

The contact time between the transition metal catalyst and the optically active form of the compound represented by Formula (1) is usually from 0.1 hours to 100 hours, and preferably from 0.1 hours to 24 hours.

By bringing the transition metal catalyst into contact with the optically active form of the compound represented by Formula (1), a mixture that contains a racemate of the compound represented by Formula (1) can be obtained. For example, by removing the catalyst from the mixture by filtration, etc., a racemate of the compound represented by Formula (1) can be collected. The obtained racemate of the compound represented by Formula (1) can also be purified according to a known method such as concentration, extraction, transfer dissolution, recrystallization, and chromatography.

The catalyst removed by filtration, etc. can be recovered and used again for production of a racemate of the compound represented by Formula (1). Examples of the recovery method include a method in which the catalyst is supported on a carrier.

The recovered catalyst is preferably washed with a solvent. Examples of the solvent include alcohol compounds such as methanol; aqueous alkali solutions such as an aqueous sodium hydroxide solution; water; and a solution of mixture thereof.

Hereinafter, the room temperature in Examples indicates 10° C. to 35° C. The optical purity in Examples was determined by means of high performance liquid chromatography analysis under the following conditions.

Columns: Daicel CHIRALCEL OD-H (4.6 mmϕ×250 mm)
Eluent: hexane/2-propanol=99/1 (v/v)
Flow rate: 0.5 mL/min
Temperature: 40° C.
Detector: UV 254 nm The recovery rate was determined by means of high performance liquid chromatography analysis under the following conditions.

Columns: Equipment for Evaluation and Study of Chemical Materials, L-Column ODS (4.6 mmϕ×150 mm)
Eluent: acetonitrile/0.1% aqueous phosphoric acid solution=30/70 (v/v) to 90/10 (v/v)
Flow rate: 1.0 mL/min
Temperature: 40° C.
Detector: UV 254 nm Example 1

Into a reaction vessel were charged 6.00 parts by weight of (3R)-1,1,3-trimethyl-4-aminoindane (optical purity of 96.5% ee), 0.81 parts by weight of 5% palladium-carbon (STD-type, manufactured by N. E. Chemcat Corporation), and 12 parts by weight of 2-propanol, thereby obtaining a mixture. The reaction vessel was sealed and the gas inside the reaction vessel was replaced with nitrogen. While stirring the mixture at room temperature, to the reaction vessel was charged hydrogen until the internal pressure of hydrogen in the reaction vessel reached 0.5 MPa. After 15 minutes, the gas in the reaction vessel was replaced with nitrogen, and the mixture was stirred at an internal temperature of 150° C. and an internal pressure of 0.8 MPa for 7 hours to obtain a reaction mixture. The obtained reaction mixture was cooled and filtered. The obtained solid was washed with 20 parts by weight of 2-propanol. The washing liquid recovered after washing and the filtrate obtained by filtration were combined. The combined mixture was concentrated under reduced pressure to obtain 5.82 parts by weight of 1,1,3-trimethyl-4-aminoindane. The obtained 1,1,3-trimethyl-4-aminoindane had an optical purity of 1.2% ee and a recovery rate of 97.0%.

Example 2

Into a reaction vessel were charged 6.00 parts by weight of (3R)-1,1,3-trimethyl-4-aminoindane (optical purity of 96.5% ee) and 1.60 parts by weight of 5% palladium-carbon (STD-type, manufactured by N. E. Chemcat Corporation), thereby obtaining a mixture. The reaction vessel was sealed, the gas in the reaction vessel was replaced with nitrogen, and then the mixture was stirred at 150° C. to obtain a reaction mixture. While stirring the obtained reaction mixture, 1.40 parts by weight of cyclohexene was added dropwise thereto over 5 hours. Thereafter, the reaction mixture was cooled and filtered. The obtained solid was washed with 20 parts by weight of 2-propanol. The washing liquid recovered after washing and the filtrate obtained by filtration were combined. The combined mixture was concentrated under reduced pressure to obtain 5.63 parts by weight of 1,1,3-trimethyl-4-aminoindane. The obtained 1,1,3-trimethyl-4-aminoindane had an optical purity of 0.29% ee and a recovery rate of 93.8%.

Example 3

Into a reaction vessel were charged 6.00 parts by weight of (3R)-1,1,3-trimethyl-4-aminoindane (optical purity of 96.5% ee) and 1.62 parts by weight of 5% palladium-carbon (STD-type, manufactured by N. E. Chemcat Corporation), thereby obtaining a mixture. The reaction vessel was sealed, the gas in the reaction vessel was replaced with nitrogen, and then the mixture was stirred at 200° C. for 7.5 hours to obtain a reaction mixture. Thereafter, the obtained reaction mixture was cooled and filtered. The obtained solid was washed with 20 parts by weight of 2-propanol. The washing liquid recovered after washing and the filtrate obtained by filtration were combined. The combined mixture was concentrated under reduced pressure to obtain 5.06 parts by weight of 1,1,3-trimethyl-4-aminoindane. The obtained 1,1,3-trimethyl-4-aminoindane had an optical purity of 3.3% ee and a recovery rate of 84.3%.

Example 4

Into a reaction vessel were charged 6.00 parts by weight of (3R)-1,1,3-trimethyl-4-aminoindane (optical purity of 96.5% ee), 0.81 part by weight of 5% palladium-carbon (STD-type, manufactured by N. E. Chemcat Corporation), and 12 parts by weight of 2-propanol, thereby obtaining a mixture. The reaction vessel was sealed and the gas in the reaction vessel was replaced with nitrogen. While stirring the mixture at room temperature, into the reaction vessel was charged hydrogen until the internal pressure of hydrogen in the reaction vessel reached 0.5 MPa. After 15 minutes, hydrogen was removed to normal pressure, and the mixture was stirred at an internal temperature of 130° C. and an internal pressure of 0.45 MPa for 7 hours while the inside of the reaction vessel was replaced with hydrogen, thereby obtaining a reaction mixture. The obtained reaction mixture was cooled and filtered. The obtained solid was washed with 20 parts by weight of 2-propanol. The washing liquid recovered after washing and the filtrate obtained by filtration were combined. The combined mixture was concentrated under reduced pressure to obtain 5.55 parts by weight of 1,1,3-trimethyl-4-aminoindane. The obtained 1,1,3-trimethyl-4-aminoindane had an optical purity of 1.2% ee and a recovery rate of 92.5%.

Example 5

Into a reaction vessel were charged 31.7 parts by weight of (3R)-1,1,3-trimethyl-4-aminoindane (optical purity of 67.0% ee) and 0.36 parts by weight of 5% palladium-alumina, thereby obtaining a mixture. The reaction vessel was sealed and the gas in the reaction vessel was replaced with nitrogen. While the mixture was stirred, into the reaction vessel was charged hydrogen until the internal pressure of hydrogen in the reaction vessel reached 0.5 MPa, and the mixture was stirred at an internal temperature of 60° C. After 1 hour, the gas in the reaction vessel was replaced with nitrogen, and the mixture was stirred at an internal temperature of 155° C. and an internal pressure of 0.1 MPa for 7 hours, thereby obtaining a reaction mixture. The obtained reaction mixture was cooled and filtered. The obtained solid was washed with 45 parts by weight of toluene. The washing liquid recovered after washing and the filtrate obtained by filtration were combined to obtain a solution of 73.4 parts by weight of 1,1,3-trimethyl-4-aminoindane in toluene. The obtained 1,1,3-trimethyl-4-aminoindane had an optical purity of 4.5% ee and a recovery rate of 98.7%.

Example 6

Into a reaction vessel were charged 31.7 parts by weight of (3R)-1,1,3-trimethyl-4-aminoindane (optical purity of 67.0% ee) and 0.76 parts by weight of 5% palladium-carbon (E-type, manufactured by N. E. Chemcat Corporation), thereby obtaining a mixture. The reaction vessel was sealed and the gas in the reaction vessel was replaced with nitrogen. While the mixture was stirred, into the reaction vessel was charged hydrogen until the internal pressure of hydrogen in the reaction vessel reached 0.5 MPa, and the mixture was stirred at an internal temperature of 60° C. After 1 hour, the gas in the reaction vessel was replaced with nitrogen, and the mixture was stirred at an internal temperature of 145° C. and an internal pressure of 0.15 MPa for 14 hours, thereby obtaining a reaction mixture. The obtained reaction mixture was cooled and filtered. The obtained solid was washed with 45 parts by weight of toluene. The washing liquid recovered after washing and the filtrate obtained by filtration were combined to obtain a solution of 73.0 parts by weight of 1,1,3-trimethyl-4-aminoindane in toluene. The combined 1,1,3-trimethyl-4-aminoindane had an optical purity of 0.7% ee and a recovery rate of 97.7%.

Example 7

Into a reaction vessel were charged 31.2 parts by weight of (3R)-1,1,3-trimethyl-4-aminoindane (optical purity of 67.0% ee) and 0.83 part by weight of 4.5% palladium-0.5% platinum-carbon (ASCA-2, manufactured by N. E. Chemcat Corporation), thereby obtaining a mixture. The reaction vessel was sealed and the gas in the reaction vessel was replaced with nitrogen. While the mixture was stirred, into the reaction vessel was charged hydrogen until the internal pressure of hydrogen in the reaction vessel reached 0.5 MPa, and the mixture was stirred at an internal temperature of 60° C. After 1 hour, the gas in the reaction vessel was replaced with nitrogen, and the mixture was stirred at an internal temperature of 180° C. and an internal pressure of 0.3 MPa for 12.5 hours, thereby obtaining a reaction mixture. The obtained reaction mixture was cooled and filtered. The obtained solid was washed with 45 parts by weight of toluene. The washing liquid recovered after washing and the filtrate obtained by filtration were combined to obtain a solution of 77.5 parts by weight of 1,1,3-trimethyl-4-aminoindane in toluene. The combined 1,1,3-trimethyl-4-aminoindane had an optical purity of 0.29% ee and a recovery rate of 97.7%.

Example 8

Into an autoclave reaction vessel were charged 104.0 parts by weight of (3R)-1,1,3-trimethyl-4-aminoindane (optical purity of 67.0% ee), 2.55 parts by weight of 5% palladium-carbon (E-type, manufactured by N. E. Chemcat Corporation), and 1.5 parts by weight of toluene, thereby obtaining a mixture. The reaction vessel was sealed and the gas in the reaction vessel was replaced with nitrogen. While the mixture was stirred, into the reaction vessel was charged hydrogen until the internal pressure of hydrogen in the reaction vessel reached 0.5 MPa, and the mixture was stirred at an internal temperature of 60° C. After 1 hour, the gas in the reaction vessel was replaced with nitrogen, and the mixture was stirred at an internal temperature of 150° C. and an internal pressure of 0.1 MPa for 14 hours, thereby obtaining a reaction mixture. The obtained reaction mixture was cooled and filtered using Celite. The obtained solid was washed with 150 parts by weight of toluene. The washing liquid recovered after washing and the filtrate obtained by filtration were combined to obtain a solution of 244.6 parts by weight of 1,1,3-trimethyl-4-aminoindane in toluene. The combined 1,1,3-trimethyl-4-aminoindane had an optical purity of 0.35% ee and a recovery rate of 98.9%. At this time, the filtered catalyst was washed twice with 30 parts by weight of methanol, 30 parts by weight of 10% caustic water, and 30 parts by weight of water twice, thereby recovering 3.84 parts by weight of palladium-carbon, including Celite.

2.88 parts by weight of the recovered palladium-carbon and 0.64 part, by weight of fresh 5% palladium-carbon (E-type, manufactured by N. E. Chemcat Corporation) were charged into an autoclave reaction vessel, and 104.0 parts by weight of (3R)-1,1,3-trimethyl-4-aminoindane (optical purity of 67.0% ee) and 1.5 parts by weight of toluene were added thereto, thereby obtaining a mixture. The reaction vessel was sealed and the gas in the reaction vessel was replaced with nitrogen. While the mixture was stirred, into the reaction vessel was charged hydrogen until the internal pressure of hydrogen in the reaction vessel reached 0.5 MPa, and the mixture was stirred at an internal temperature of 60° C. After 1 hour, the gas in the reaction vessel was replaced with nitrogen, and the mixture was stirred at an internal temperature of 150° C. and an internal pressure of 0.1 MPa for 14 hours, thereby obtaining a reaction mixture. The obtained reaction mixture was cooled and filtered using Celite. The obtained solid was washed with 150 parts by weight of toluene. The washing liquid recovered after washing and the filtrate obtained by filtration were combined to obtain a solution of 244.6 parts by weight of 1,1,3-trimethyl-4-aminoindane in toluene. The combined 1,1,3-trimethyl-4-aminoindane had an optical purity of 0.11% ee and a recovery rate of 98.5%.

INDUSTRIAL APPLICABILITY

According to the present invention, a racemate can be efficiently produced from an optically active form of the compound represented by Formula (1).

The invention claimed is:

1. A method for producing a racemate of a compound represented by Formula (1), comprising bringing a transition metal catalyst into contact with an optically active form of the compound represented by Formula (1):

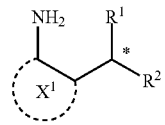

(1)

[in Formula (1),
a ring $X^1$ represents an aromatic ring;
$R^1$ represents a $C_{1-6}$ alkyl group, a $C_{3-8}$ cycloalkyl group, or a $C_{1-6}$ halo-alkyl group;
$R^2$ is a group different from $R^1$ and represents a $C_{1-6}$ alkyl group, a $C_{3-8}$ cycloalkyl group, or a $C_{1-6}$ halo-alkyl group, or $R^2$ and the ring $X^1$ are bonded to each other to form a ring;
a hydrogen atom(s) of the ring $X^1$ is optionally replaced with a $C_{1-6}$ alkyl group, a $C_{1-6}$ halo-alkyl group, a cyano group, a nitro group, a $C_{1-6}$ alkoxy group, or a halogen atom; and
* represents an asymmetric carbon atom].

2. The production method according to claim 1, wherein the compound represented by Formula (1) is a compound represented by Formula (1a):

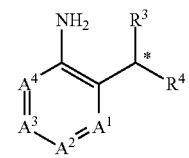

(1a)

[in Formula (1 a),
$A^1$, $A^2$, A $A^3$, and $A^4$ each independently represent —N═ or —C($R^a$)═, and $R^a$ represents a hydrogen atom, a $C_{1-6}$ alkyl group, a $C_{1-6}$ halo-alkyl group, a cyano group, a nitro group, a $C_{1-6}$ alkoxy group, or a halogen atom;
$R^3$ represents a $C_{1-6}$ alkyl group, a $C_{3-8}$ cycloalkyl group, or a $C_{1-6}$ halo-alkyl group;
$R^4$ is a group different from $R^3$ and represents a $C_{1-6}$ alkyl group, a $C_{3-8}$ cycloalkyl group, or a $C_{1-6}$ halo-alkyl group, or when $A^1$ represents —C($R^a$)═, $R^4$ and $R^a$ are optionally bonded to each other form a divalent hydrocarbon group, and hydrogen atoms of the hydrocarbon group are optionally replaced with a halogen atom, and —CH$_2$— of the hydrocarbon group is optionally replaced with —O—;
two $R^a$'s of the adjacent —C($R^a$)═'s are optionally bonded to each other to form a benzene ring together with a carbon atom to which each of them is bonded, and a hydrogen atom(s) of the benzene ring are optionally replaced with a $C_{1-6}$ alkyl group or a halogen atom; and
* represents an asymmetric carbon atom].

3. The production method according to claim 2, wherein $A^1$, $A^2$, $A^3$, and $A^4$ are C($R^a$)═.

4. The production method according to claim 2, wherein $A^1$ is —C($R^a$)═, and $R^a$ and $R^4$ are bonded to each other to form a divalent hydrocarbon group.

5. The production method according to claim 2, wherein the compound represented by Formula (1a) is a compound represented by Formula (2):

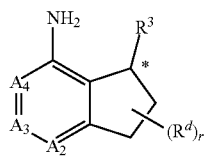

(2)

[in Formula (2), $A^2$, $A^3$, and $A^4$ each independently represent —N= or —C($R^a$)=, $R^a$ represents a hydrogen atom, a $C_{1-6}$ alkyl group, a $C_{1-6}$ halo-alkyl group, or a halogen atom, and $R^3$ represents a $C_{1-6}$ alkyl group;

$R^d$ represents a $C_{1-6}$ alkyl group, or a $C_{1-6}$ halo-alkyl group, r represents an integer of 0 to 4, and when r is an integer of 2 or more, a plurality of $R^d$'s are optionally the same or different; and

* represents an asymmetric carbon atom].

6. The production method according to claim 2, wherein $R^3$ is a $C_{1-6}$ alkyl group.

7. The production method according to claim 1, wherein the compound represented by Formula (1) is 1,1,3-trimethyl-4-aminoindane represented by Formula (3):

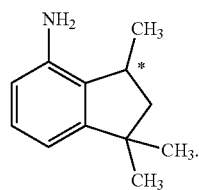

(3)

8. The production method according to claim 1, wherein the transition metal catalyst is a hydrogen-absorbing transition metal catalyst having absorbed hydrogen therein.

9. The production method according to claim 1, wherein the transition metal catalyst is a palladium catalyst.

10. The production method according to claim 9, wherein the palladium catalyst is
a palladium-carbon catalyst.

11. A method for racemizing a compound represented by Formula (1), comprising
bringing a transition metal catalyst into contact with an optically active form of the compound represented by Formula (1):

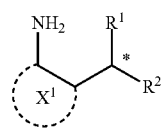

(1)

[in Formula (1), a ring $X^1$ represents an aromatic ring;

$R^1$ represents a $C_{1-6}$ alkyl group, a $C_{3-8}$ cycloalkyl group, or a $C_{1-6}$ halo-alkyl group;

$R^2$ is a group different from $R^1$ and represents a $C_{1-6}$ alkyl group, a $C_{3-8}$ cycloalkyl group, or a $C_{1-6}$ halo-alkyl group, or $R^2$ and the ring $X^1$ are bonded to each other to form a ring;

a hydrogen atom(s) of the ring $X^1$ is optionally replaced with a $C_{1-6}$ alkyl group, a $C_{1-6}$ halo-alkyl group, a cyano group, a nitro group, a $C_{1-6}$ alkoxy group, or a halogen atom; and

* represents an asymmetric carbon atom].

* * * * *